United States Patent
Jolly et al.

(10) Patent No.: US 10,888,507 B2
(45) Date of Patent: Jan. 12, 2021

(54) COSMETIC OR DERMATOLOGICAL COMPOSITION COMPRISING A MEROCYANINE AND AN OILY PHASE COMPRISING AT LEAST ONE N-SUBSTITUTED AMIDE

(71) Applicant: L'OREAL, Paris (FR)

(72) Inventors: Yannick Jolly, Chevilly la Rue (FR); Didier Candau, Chevilly la Rue (FR); Mahassine Safouane, Chevilly la Rue (FR); Angelina Roudot, Chevilly la Rue (FR)

(73) Assignee: L'OREAL, Paris (FR)

( * ) Notice: Subject to any disclaimer, the term of this patent is extended or adjusted under 35 U.S.C. 154(b) by 14 days.

(21) Appl. No.: 16/072,679

(22) PCT Filed: Jan. 26, 2017

(86) PCT No.: PCT/EP2017/051631
§ 371 (c)(1),
(2) Date: Jul. 25, 2018

(87) PCT Pub. No.: WO2017/129670
PCT Pub. Date: Aug. 3, 2017

(65) Prior Publication Data
US 2018/0369100 A1 Dec. 27, 2018

(30) Foreign Application Priority Data
Jan. 26, 2016 (FR) .................... 16 50623

(51) Int. Cl.
| | |
|---|---|
| A61K 8/42 | (2006.01) |
| A61K 8/44 | (2006.01) |
| A61K 8/49 | (2006.01) |
| A61Q 17/04 | (2006.01) |
| A61K 8/41 | (2006.01) |

(52) U.S. Cl.
CPC .................. *A61K 8/42* (2013.01); *A61K 8/41* (2013.01); *A61K 8/44* (2013.01); *A61K 8/4926* (2013.01); *A61K 8/4973* (2013.01); *A61Q 17/04* (2013.01); *A61K 2800/592* (2013.01)

(58) Field of Classification Search
None
See application file for complete search history.

(56) References Cited

U.S. PATENT DOCUMENTS 8,535,648 B2 * 9/2013 Wagner ............... A61K 8/35
424/59
8,829,192 B2 * 9/2014 Wagner ............... A61K 8/466
546/184

FOREIGN PATENT DOCUMENTS

| | | |
|---|---|---|
| JP | 2010516725 A | 5/2010 |
| WO | WO-2008/090066 A2 | 7/2008 |
| WO | WO-2014/111568 A1 | 7/2014 |
| WO | WO 2014/111570 A2 * | 7/2014 ............... A61K 8/41 |

* cited by examiner

*Primary Examiner* — Brian J Davis
(74) *Attorney, Agent, or Firm* — Polsinelli PC

(57) ABSTRACT

The present invention relates to a composition, in particular a cosmetic or dermatological composition, comprising, in a physiologically acceptable medium: a) at least one merocyanine of formula (1) or (2) b) at least one oily phase comprising at least one N-substituted amide of formula (4): The present invention also relates to a non-therapeutic cosmetic process for caring for and/or making up a keratin material, comprising the application, to the surface of said keratin material, of at least one composition as defined above. The invention also relates to a non-therapeutic cosmetic process for limiting the darkening of the skin and/or improving the colour and/or uniformity of the complexion, comprising the application, to the surface of the keratin material, of at least one composition as defined previously. The present invention also relates to a non-therapeutic cosmetic process for preventing and/or treating the signs of ageing of a keratin material, comprising the application, to the surface of the keratin material, of at least one composition as defined previously.

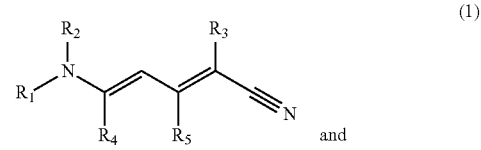

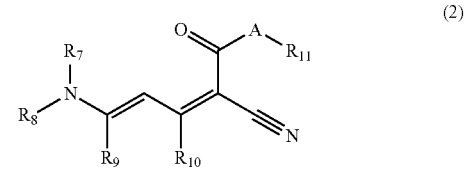

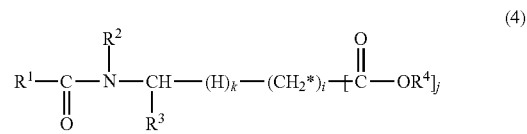

21 Claims, No Drawings

COSMETIC OR DERMATOLOGICAL
COMPOSITION COMPRISING A
MEROCYANINE AND AN OILY PHASE
COMPRISING AT LEAST ONE
N-SUBSTITUTED AMIDE

CROSS REFERENCE TO RELATED
APPLICATIONS

This application is the National Phase of Application No. PCT/EP2017/051631 filed Jan. 26, 2017, which claims priority to Application No. 16 50623 filed in France on Jan. 26, 2016 under 35 U.S.C. § 119. The entire contents of each application are hereby incorporated by reference.

The present invention relates to a cosmetic or dermatological composition comprising, in a physiologically acceptable medium:
  a) at least one merocyanine of formula (1) or (2) that will be defined below in detail and
  b) at least one oily phase comprising at least one particular N-substituted amide.

The present invention also relates to a non-therapeutic cosmetic process for caring for and/or making up a keratin material, comprising the application, to the surface of said keratin material, of at least one composition according to the invention as defined above.

The invention also relates to a non-therapeutic cosmetic process for limiting the darkening of the skin and/or improving the colour and/or uniformity of the complexion, comprising the application, to the surface of the keratin material, of at least one composition as defined previously.

The present invention also relates to a non-therapeutic cosmetic process for preventing and/or treating the signs of ageing of a keratin material, comprising the application, to the surface of the keratin material, of at least one composition as defined previously.

It is known that radiation with wavelengths of between 280 nm and 400 nm makes possible tanning of the human epidermis and that radiation with wavelengths of between 280 and 320 nm, known under the name of UV-B rays, harms the development of a natural tan. Exposure is also capable of bringing about a detrimental change in the biomechanical properties of the epidermis which is reflected by the appearance of wrinkles, leading to premature ageing of the skin.

It is also known that UV-A rays with wavelengths of between 320 and 400 nm penetrate more deeply into the skin than UV-B rays. UV-A rays cause immediate and persistent browning of the skin. Daily exposure to UVA rays, even of short duration, under normal conditions can result in damage to the collagen fibres and the elastin, which is reflected by a modification to the microrelief of the skin, the appearance of wrinkles and uneven pigmentation (liver spots, heterogeneity of the complexion).

Protection against UVA and UVB radiation is therefore necessary. An effective photoprotective product must protect against both UVA and UVB radiation.

Many photoprotective compositions have been proposed to date to overcome the effects induced by UVA and/or UVB radiation. They generally contain organic UV-screening agents and/or inorganic UV-screening agents, which function according to their own chemical nature and according to their own properties by absorption, reflection or scattering of the UV radiation. They generally contain mixtures of liposoluble organic screening agents and/or of water-soluble UV-screening agents combined with metal oxide pigments such as titanium dioxide or zinc oxide.

Many cosmetic compositions intended to limit darkening of the colour of the skin, and to improve the colour and uniformity of the complexion have been proposed to date. It is well known in the field of suntan products that such compositions can be obtained by using UV-screening agents, and in particular UVB-screening agents. Some compositions may also contain UVA-screening agents. This screening system must cover UVB protection for the purpose of limiting and controlling the neo-synthesis of melanin promoting overall pigmentation, but must also cover UVA protection in order to limit and control the oxidation of the already existing melanin resulting in darkening of the colour of the skin.

However, it is extremely difficult to find a composition containing a particular combination of UV-screening agents that would be speciallly suitable for photoprotection of the skin and particularly for an improvement in the quality of the skin both in terms of the colour and in terms of its mechanical elasticity properties.

Advantageously, this improvement is particularly desired on skin that is already pigmented, for the purpose of not increasing either the pigmentary melanin load or the structure of the melanin already present within the skin.

In fact, the majority of organic UV-screening agents are constituted of aromatic compounds which absorb in the wavelength range between 280 and 370 nm. In addition to their solar radiation-screening capacity, the desired photoprotective compounds must also have good cosmetic properties, good solubility in the usual solvents and in particular in fatty substances such as oils, and also good photostability alone or in combination with other UV-screening agents. They must also be colourless or at least have a colour that is cosmetically acceptable for consumers.

One of the main drawbacks known to date of these compositions is that these screening systems have insufficient efficiency against UV radiation and particularly against long UVA radiation with wavelengths above 370 nm with the aim of controlling photoinduced pigmentation and the evolution thereof by means of a system which screens out UV radiation over the whole of the UV spectrum.

Among all the compounds that have been recommended for this purpose, an advantageous family of UV-screening agents which is constituted of carbonated merocyanine derivatives has been proposed, which is described in U.S. Pat. No. 4,195,999, application WO 2004/006878 and document IP COM Journal 4 (4), 16 No. IPCOM000011179D published on Apr. 3, 2004. These compounds have very good screening properties in the long UVA radiation range, but have poorly satisfactory solubility in the usual solvents and in particular in fatty substances such as oils, and an unsatisfactory photostability for some merocyanines.

With the aim of searching for other merocyanines which have better solubility in the usual solvents and better photostability, application WO 2013/011094 has proposed merocyanines comprising polar groups constituted of hydroxyl and ether functions, which show good long UVA-screening efficiency. However, the oil-solubility of these particular merocyanines is not yet entirely satisfactory, and often requires a fastidious formulating process. Moreover, the large amounts of solvent that are required in order to dissolve this type of merocyanine may lead to cosmetic displeasures such as a tacky and greasy effect on application.

There thus remains the need to improve the solubility of these merocyanines in photoprotective formulations comprising at least one oily phase.

The applicant has discovered, surprisingly, that by using particular N-substituted amides, it is possible to substantially improve the solubility of these merocyanines in an oily phase. This discovery forms the basis of the present invention.

Thus, in accordance with one of the subjects of the present invention, a composition, in particular a cosmetic or dermatological composition, is now provided which comprises, in a physiologically acceptable medium:
  a) at least one merocyanine of formula (1) or (2) that will be defined below in detail and
  b) at least one oily phase comprising at least one N-substituted amide of formula (4) below:

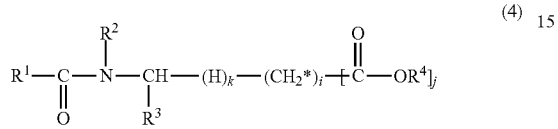

Moreover, there also remains the need to improve the solubility of merocyanines in the presence of organic screening agents. Indeed, the addition of additional screening agents can destabilize compositions comprising a merocyanine.

The applicant has discovered, surprisingly, that by using particular N-substituted amides, it is possible to substantially improve the solubility of these merocyanines in an oily phase in the presence of additional organic UV-screening agents.

The present invention also relates to a non-therapeutic cosmetic process for caring for and/or making up a keratin material, comprising the application, to the surface of said keratin material, of at least one composition according to the invention as defined above.

The invention also relates to a non-therapeutic cosmetic process for limiting the darkening of the skin and/or improving the colour and/or uniformity of the complexion, comprising the application, to the surface of the keratin material, of at least one composition as defined previously.

The present invention also relates to a non-therapeutic cosmetic process for preventing and/or treating the signs of ageing of a keratin material, comprising the application, to the surface of the keratin material, of at least one composition as defined previously.

Other characteristics, aspects and advantages of the invention will become apparent on reading the detailed description which follows.

The term "keratin materials" is intended to mean the skin (of the body, face and around the eyes), hair, eyelashes, eyebrows, body hair, nails, lips or mucous membranes.

The term "physiologically acceptable" is intended to mean compatible with the skin and/or its integuments, which has a pleasant colour, odour and feel, and which does not cause any unacceptable discomfort (stinging, tautness or redness) liable to put the consumer off using this composition.

The term "between X and Y" is intended to mean the range of values also including the limits X and Y.

The term "preventing" or "prevention" is intended to mean, according to the invention, reducing the risk of occurrence or slowing down the occurrence of a given phenomenon, namely, according to the present invention, the signs of ageing of a keratin material.

Merocyanines

According to the present invention, the merocyanine compounds in accordance with the invention correspond to formula (1) or (2) below

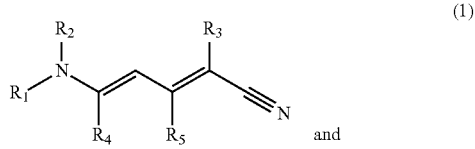

and

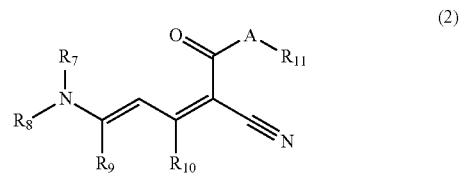

in which:
$R_1$ and $R_2$, independently of one another, are hydrogen; a $C_1$-$C_{22}$ alkyl group, a $C_2$-$C_{22}$ alkenyl group, or a $C_2$-$C_{22}$ alkynyl group, these groups possibly being substituted with at least one hydroxyl group or else interrupted with at least one —O—; or else $R_1$ and $R_2$ form, together with the nitrogen atom which links them, a —$(CH_2)_n$— ring which may be optionally interrupted with —O— or —NH—;
$R_3$ is a —(C=O)$OR_6$ group; or a —(CO)$NHR_6$ group;
$R_6$ is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, said groups possibly being substituted with one or more OH;
$R_4$ and $R_5$ are hydrogens; or $R_4$ and $R_5$ form a —$(CH_2)_n$— ring which may be substituted with a $C_1$-$C_4$ alkyl group and/or interrupted with one or more —O— or with —NH—;
n is a number between 2 and 7;
$R_7$ and $R_8$, independently of one another, are hydrogen; a $C_1$-$C_{22}$ alkyl group, a $C_2$-$C_{22}$ alkenyl group, a $C_2$-$C_{22}$ alkynyl group, said groups possibly being interrupted with one or more O and/or substituted with one or more OH; a $C_3$-$C_{22}$ cycloalkyl group or a $C_3$-$C_{22}$ cycloalkenyl group, said groups possibly being interrupted with one or more —O—;
or else $R_7$ and $R_8$ form, together with the nitrogen which links them, a —$(CH_2)_n$— ring which may be interrupted with one or more —O—;
$R_9$ and $R_{10}$ are hydrogen; or $R_9$ and $R_{10}$ form a —$(CH_2)_n$— ring potentially substituted with a $C_1$-$C_4$ alkyl and/or interrupted with an —O— or —NH—;
A is —O—; or —NH;
$R_{11}$ is a $C_1$-$C_{22}$ alkyl group; a $C_2$-$C_{22}$ alkenyl group; a $C_2$-$C_{22}$ alkynyl group; a $C_3$-$C_{22}$ cycloalkyl group or a $C_3$-$C_{22}$ cycloalkenyl group, said groups possibly being interrupted with one or more O; or a $C_1$-$C_{22}$ alkyl group or a $C_2$-$C_{22}$ alkenyl group which is substituted with a $C_3$-$C_{22}$ cycloalkyl group or a $C_3$-$C_{22}$ cycloalkenyl group, said $C_3$-$C_{22}$ cycloalkyl group or $C_3$-$C_{22}$ cycloalkenyl group possibly being interrupted with one or more —O—.

Preferably, the compounds of formula (1) or (2) have the following characteristics:
(I) at least one of the $R_1$, $R_2$ or $R_6$ groups is substituted with a hydroxyl;
(II) if one of the $R_1$ denotes a hydroxyethyl, $R_2$ does not denote a hydrogen, a methyl or an ethyl or a hydroxyethyl; and if $R_1$ denotes hydrogen, $R_2$ is not 1-hydroxy-3-methylbut-2-yl;

(III) if $R_6$ is substituted with one or more OH, one of $R_1$ or $R_2$ is a $C_4$-$C_{22}$ alkyl group; or else $R_1$ and $R_2$ form, together with the nitrogen to which they are bonded, a piperidyl or morpholinyl radical;

(IV) at least one among the $R_7$, $R_8$ or $R_{11}$ radicals is interrupted with one or more —O—.

The preferred compounds are those of formula (1) or (2) wherein:

$R_1$ and $R_2$, independently of one another, are hydrogen, a $C_4$-$C_{12}$ alkyl group; or a $C_3$-$C_{12}$ hydroxyalkyl group; or at least one of $R_1$ or $R_2$ is a $C_3$-$C_{12}$ hydroxyalkyl and $R_3$, $R_4$ and $R_5$ have the same meanings indicated previously.

The preferred compounds are also those of formula (1) wherein:

$R_6$ is a $C_1$-$C_{12}$ alkyl group, which may be substituted with one or more hydroxyls.

The compounds which are the most preferential are also those of formula (1), wherein:

$R_6$ is a $C_1$-$C_{12}$ alkyl group, which may be substituted with one or more hydroxyls; one of the $R_1$ or $R_2$ radicals is a $C_4$-$C_{22}$ alkyl group; or else $R_1$ and $R_2$ form, together with the nitrogen which links them, a —(CH$_2$)$_n$— ring which may be interrupted with —O— and/or —NH—; and $R_4$ and $R_5$ and n have the same meanings indicated previously.

The preferred compounds are those of formula (2) wherein:

$R_{11}$ is a —(CH$_2$)$_m$—O—$R_{12}$ radical, wherein $R_{12}$ is a $C_1$-$C_{12}$ alkyl group; or a $C_1$-$C_6$ alkoxy-$C_1$-$C_6$ alkyl group;

m is a number from 1 to 5; and $R_7$, $R_8$, $R_9$, $R_{10}$ and A have the same meanings indicated previously.

The compounds which are even more preferential are those of formula (1) or (2), wherein:

on the one hand, $R_1$ and $R_2$ and, on the other hand, $R_7$ and $R_8$ respectively form, together with the nitrogen atom to which they are respectively bonded, a piperidyl radical or a morpholinyl radical.

The preferred compounds are also those of formulae (1) and (2), wherein:

$R_4$ and $R_5$ and $R_9$ and $R_{10}$ respectively form a carbon-based ring which contains 6 carbon atoms.

The compounds which are the most preferential are those of formula (1), wherein:

$R_1$ and $R_2$, independently of one another, are a hydrogen; or a $C_1$-$C_{22}$ alkyl group; or a $C_1$-$C_{22}$ hydroxyalkyl group; or $R_1$ and $R_2$ form, together with the nitrogen to which they are bonded, a piperidyl or morpholinyl radical;

$R_3$ is a —(C=O)OR$_6$ group; or a —(CO)NHR$_6$ group;

$R_6$ is a $C_1$-$C_{22}$ alkyl group, which may be substituted with one or more —OH;

$R_4$ and $R_5$ are a hydrogen; or $R_4$ and $R_5$ are linked together to form a carbon-based ring which contains 6 carbon atoms.

The compounds which are the most preferential are those of formula (1), wherein:

$R_1$ and $R_2$, independently of one another, are a hydrogen, or a $C_1$-$C_{22}$ hydroxyalkyl; wherein at least one of the $R_1$ and $R_2$ radicals is a $C_1$-$C_{22}$ hydroxyalkyl group;

$R_3$ is a —(C=O)OR$_6$ group; or a —(C=O)NHR$_6$ group;

$R_6$ is a $C_1$-$C_{22}$ alkyl group; and $R_4$ and $R_5$ are hydrogens; or $R_4$ and $R_5$ are bonded together to form a carbon-based ring which contains 6 carbon atoms.

The compounds which are the most preferential are those of formula (2), wherein:

$R_7$ and $R_8$, independently of one another, are a hydrogen or a $C_1$-$C_8$ alkyl group, which may be interrupted with one or more —O—;

A is —O— or —NH;

$R_{11}$ is a $C_1$-$C_{22}$ alkyl; and $R_9$ and $R_{10}$ are a hydrogen; or $R_9$ and $R_{10}$ are bonded together to form a carbon-based ring which contains 6 carbon atoms.

The compounds which are the most preferential are those of formula (2), wherein:

$R_7$ and $R_8$ form, together with the nitrogen atom to which they are bonded, a morpholinyl or piperidyl radical;

A is —O— or —NH;

$R_{11}$ is a $C_1$-$C_{22}$ alkyl group, which may be interrupted with one or more —O—; and $R_9$ and $R_{10}$ are hydrogens; or $R_9$ and $R_{10}$ are bonded together to form a carbon-based ring which contains 6 carbon atoms.

The compounds which are even more preferential are those of formula (2), wherein:

$R_{11}$ is a —(CH$_2$)$_m$—O—$R_{12}$ radical, wherein $R_{12}$ is a $C_1$-$C_4$ alkyl group; or a $C_1$-$C_4$ alkoxy-$C_1$-$C_4$ alkyl group;

m is a number from 1 to 3; and $R_7$ and $R_8$, independently of one another, are a hydrogen; or a $C_1$-$C_{12}$ alkyl group, which may be interrupted with one or more O; or $R_7$ and $R_8$ form, together with the nitrogen atom to which they are bonded, a morpholinyl or piperidyl radical;

$R_9$ and $R_{10}$ are hydrogens or together form a carbon-based ring which contains 6 carbon atoms; and A is —O— or —NH.

The merocyanine compounds of the invention may be in the E/E-, E/Z- or Z/Z geometrical isomer form.

The alkyl, cycloalkyl, alkenyl, alkylidene or cycloalkenyl chains may be linear or branched, monocyclic or polycyclic chains.

A $C_1$-$C_{22}$ alkyl group is for example a methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

A substituted alkyl group is for example a methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-(2,4-di-tert-amylphenoxy)propyl, ethoxycarbonylmethyl-2-(2-hydroxyethoxy)ethyl or 2-furylethyl.

A hydroxy-substituted alkyl group is for example a hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl.

A $C_2$-$C_{22}$ alkenyl group is for example a linear $C_2$-$C_{12}$ alkenyl chain or preferentially a branched $C_3$-$C_{12}$ alkenyl. A $C_2$-$C_{22}$ alkenyl is for example a vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the various isomers of hexenyl, octenyl, noenyl, decenyl or dodecenyl.

A $C_3$-$C_{12}$ cycloalkyl group is for example a cyclopropyl, cyclobutyl, cyclopentyl or tri methylcyclohexyl or preferentially a cyclohexyl.

Examples of merocyanines according to the present invention are listed in Table A:

TABLE A

| Compound | Structure |
|---|---|
| 1 | Ethyl 2-cyano-5-[bis(2-methoxyethyl)amino]penta-2,4-dienoate |
| 2 | 2-Methoxyethyl 2-cyano-5-[bis(2-methoxyethyl)amino]penta-2,4-dienoate |
| 3 | 2-Ethoxyethyl 2-cyano-5-[bis(2-methoxyethyl)amino]penta-2,4-dienoate |
| 4 | 2-Ethoxyethyl 2-cyano-5-(piperidin-1-yl)penta-2,4-dienoate |
| 5 | 2-(2-Methoxyethoxy)ethyl 2-cyano-5-(piperidin-1-yl)penta-2,4-dienoate |
| 6 | 2-Cyano-N-(2-hydroxyethyl)-5-(piperidin-1-yl)penta-2,4-dienamide |
| 7 | 2,3-Dihydroxypropyl 2-cyano-5-(piperidin-1-yl)penta-2,4-dienoate |

TABLE A-continued

| Compound | Structure |
| --- | --- |
| 8 | 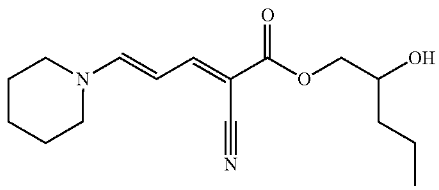 [SMILES: CCCC(O)COC(=O)/C(C#N)=C/C=C/N1CCCCC1] |
| 9 | 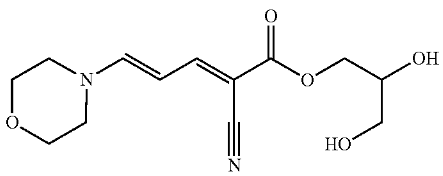 [SMILES: N#C/C(=C\C=C\N1CCOCC1)C(=O)OCC(O)CO] |
| 10 | 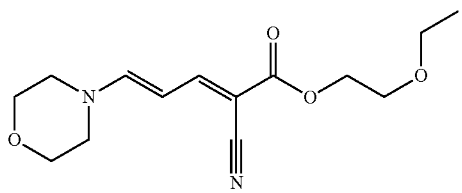 [SMILES: CCOCCOC(=O)/C(C#N)=C/C=C/N1CCOCC1] |
| 11 | 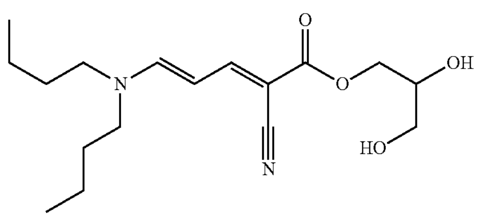 [SMILES: CCCCN(/C=C/C=C(\C#N)C(=O)OCC(O)CO)CCCC] |
| 12 | 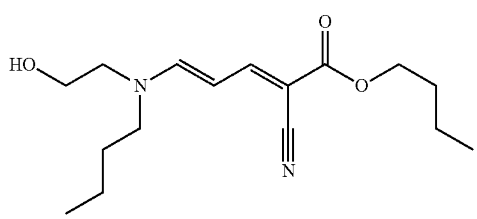 [SMILES: CCCCOC(=O)/C(C#N)=C/C=C/N(CCO)CCCC] |
| 13 | 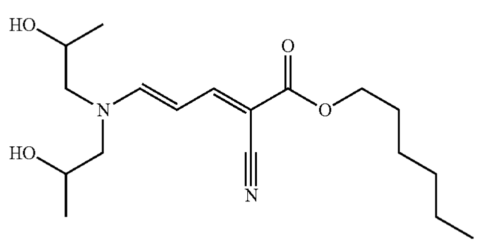 [SMILES: CCCCCCOC(=O)/C(C#N)=C/C=C/N(CC(C)O)CC(C)O] |
| 14 | 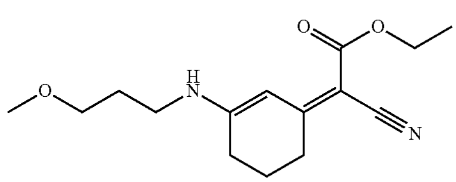 [SMILES: CCOC(=O)/C(C#N)=C1\C=C(NCCCOC)CCC1] |

TABLE A-continued

| Compound | Structure |
|---|---|
| 15 | 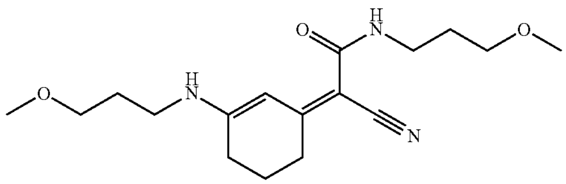 |
| 16 | 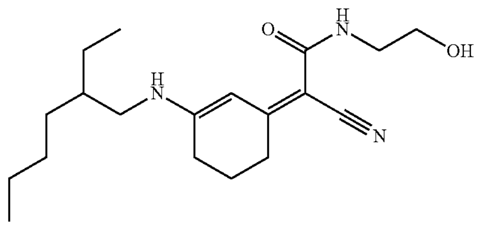 [SMILES: CCCCC(CC)CNC1=C/C(=C(/C#N)C(=O)NCCO)CCC1] |
| 17 | 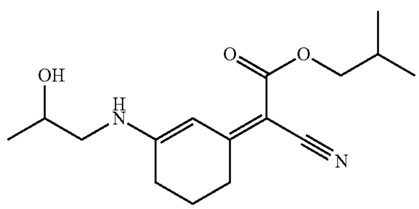 [SMILES: CC(C)COC(=O)/C(C#N)=C1\C=C(NCC(C)O)CCC1] |
| 18 | 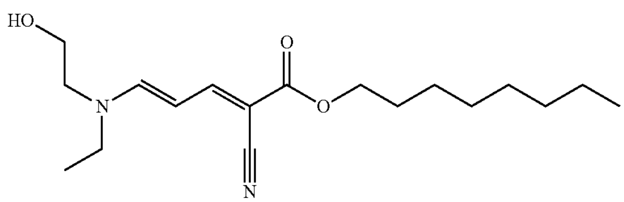 [SMILES: CCCCCCCCOC(=O)/C(C#N)=C/C=C/N(CC)CCO] |
| 19 | 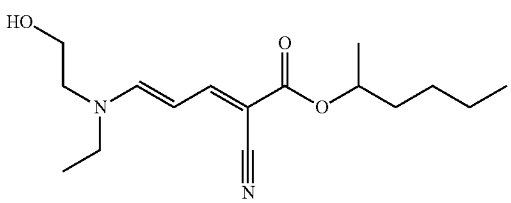 [SMILES: CCCCC(C)OC(=O)/C(C#N)=C/C=C/N(CC)CCO] |
| 20 | 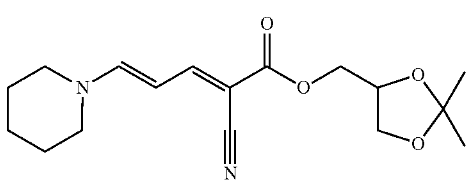 [SMILES: CC1(C)OCC(COC(=O)/C(C#N)=C/C=C/N2CCCCC2)O1] |
| 21 | 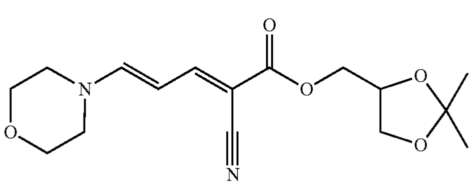 [SMILES: CC1(C)OCC(COC(=O)/C(C#N)=C/C=C/N2CCOCC2)O1] |
| 22 | 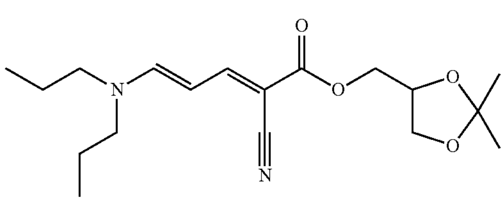 [SMILES: CCCN(/C=C/C=C(\C#N)C(=O)OCC1COC(C)(C)O1)CCC] |

TABLE A-continued
| Compound | Structure |
|---|---|
| 23 | 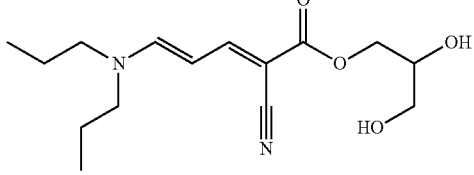 |
| 24 | 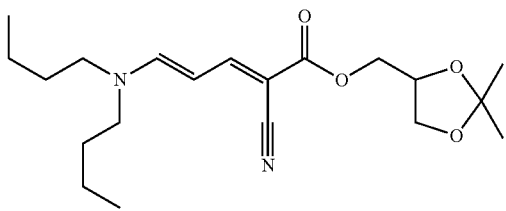 [SMILES: CCCCN(/C=C/C=C(\C#N)C(=O)OCC1COC(C)(C)O1)CCCC] |
| 25 | 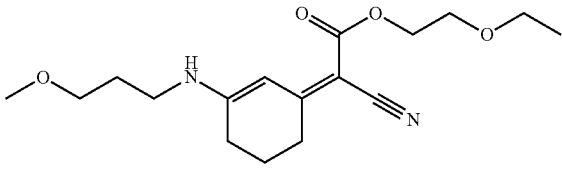 [SMILES: CCOCCOC(=O)/C(C#N)=C1\C=C(NCCCOC)CCC1] |
| 26 | 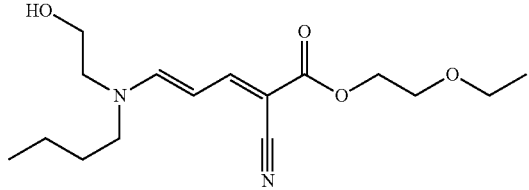 [SMILES: CCCCN(/C=C/C=C(\C#N)C(=O)OCCOCC)CCO] |
| 27 | 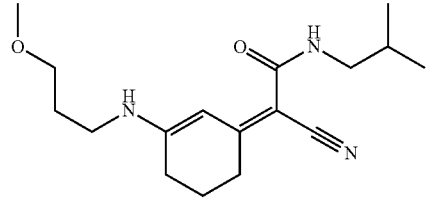 [SMILES: COCCCNC1=C/C(=C(/C#N)C(=O)NCC(C)C)CCC1] |
| 28 | 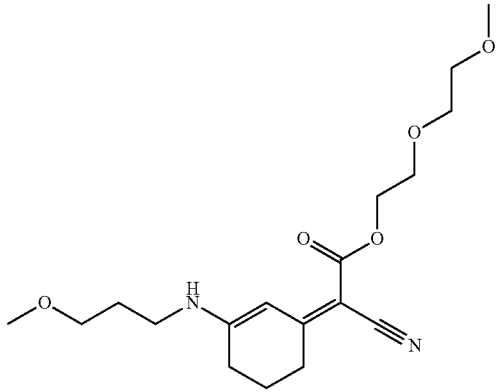 |

TABLE A-continued

| Compound | Structure |
|---|---|
| 29 | (structure) |
| 30 | (structure) |
| 31 | (structure) |
| 32 | (structure) |
| 33 | (structure) |
| 34 | (structure) |
| 35 | (structure) |

TABLE A-continued

| Compound | Structure |
|---|---|
| 36 | (structure) |
| 37 | (structure) |
| 38 | (structure) |
| 39 | (structure) |
| 40 | (structure) |
| 41 | (structure) |
| 42 | (structure) |

TABLE A-continued
| Compound | Structure |
|---|---|
| 43 | 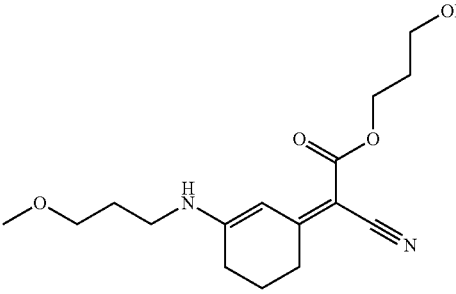 |
| 44 | 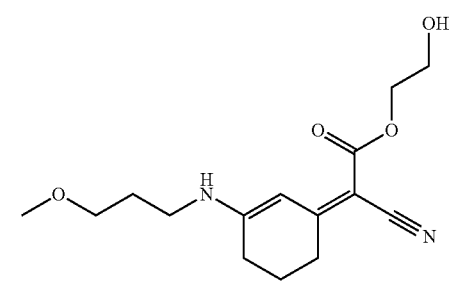 |
| 45 | 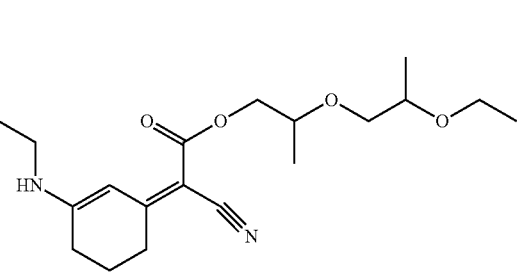 |
| 46 | 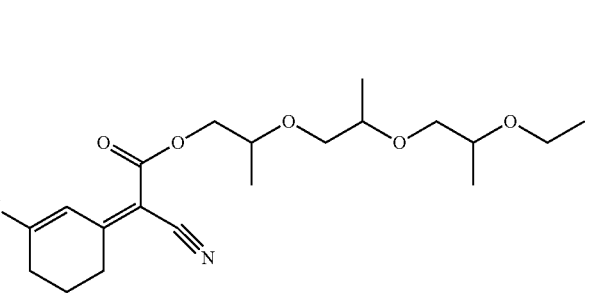 |
| 47 | 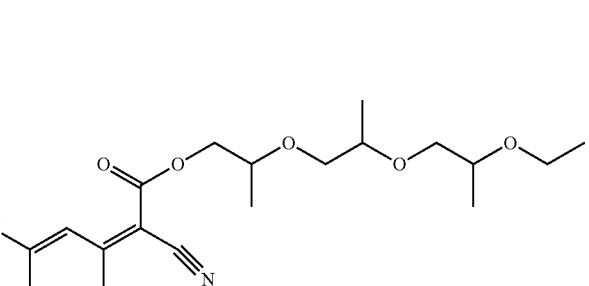 |

According to one particularly preferred form of the invention, use will be made of a family of merocyanines corresponding to formula (3) below, and also the E/E- or E/Z-geometrical isomer forms thereof:

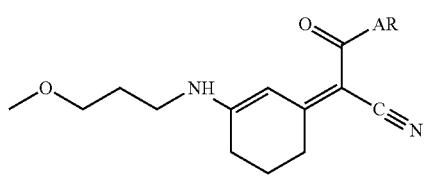
(3)

in which

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, said groups possibly being interrupted with one or more O.

The merocyanine compounds of the invention may be in their E/E- or E/Z-geometrical isomer forms:

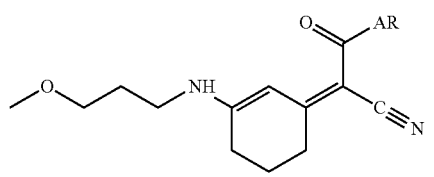

or

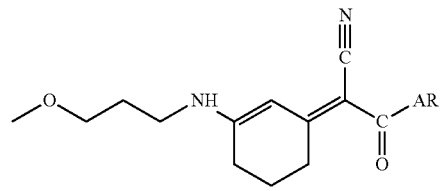

The compounds of formula (3) that are even more preferential are those wherein:

A is —O—; R is a $C_1$-$C_{22}$ alkyl, which may be interrupted with one or more O.

Among the compounds of formula (3), use will more particularly be made of those chosen from the following group and also their E/E- or E/Z-geometrical isomer forms:

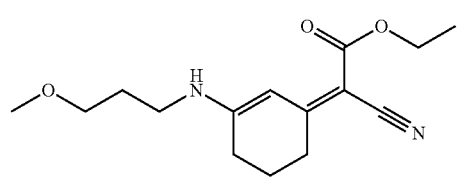

14 ethyl (2Z)-cyano{3-[(3-methoxypropyl)amino]cyclohex-2-en-1-ylidene}ethanoate

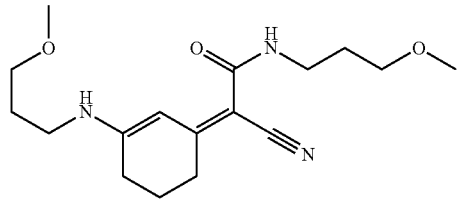

15

(2Z)-2-cyano-N-(3-methoxypropyl)-2-{3-[(3-methoxypropyl)amino]cyclohex-2-en-1-ylidene}ethanamide

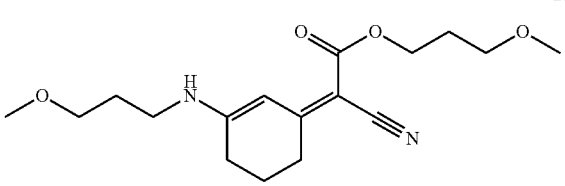

25

2-ethoxyethyl (2Z)-cyano{3-[(3-methoxypropyl)amino]cyclohex-2-en-1-ylidene}ethanoate

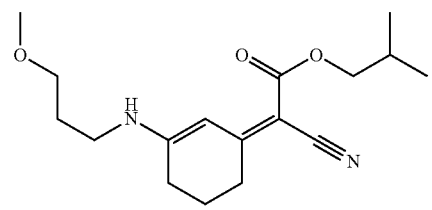

27

2-methylpropyl (2Z)-cyano{3-[(3-methoxypropyl)amino]cyclohex-2-en-1-ylidene}ethanoate

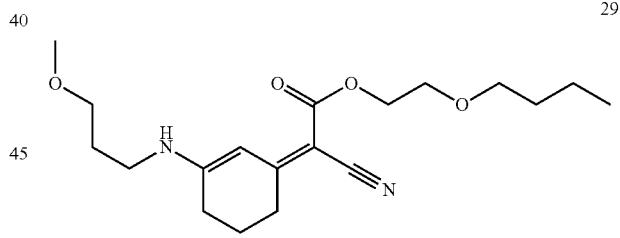

29

2-butoxyethyl (2Z)-cyano{3-[(3-methoxypropyl)amino]cyclohex-2-en-1-ylidene}ethanoate

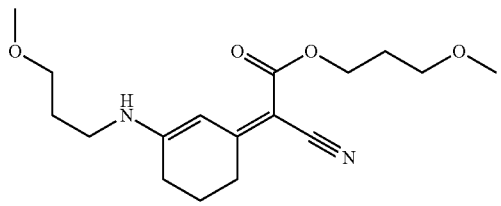 [SMILES: COCCCNC1=C/C(=C(/C#N)C(=O)OCCCOC)CCC1]

31

3-methoxypropyl (2Z)-cyano{3-[(3-methoxypropyl)amino]cyclohex-2-en-1-ylidene}ethanoate -continued

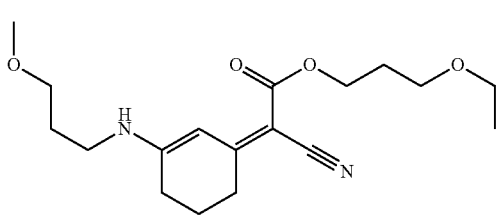 [SMILES: CCOCCCOC(=O)/C(C#N)=C1\C=C(NCCCOC)CCC1]

3-ethoxypropyl (2Z)-cyano{3-[(3-methoxypropyl)amino]cyclohex-2-en-1-ylidene}ethanoate According to one more particularly preferred mode of the invention, use will be made of the compound 2-ethoxyethyl (2Z)-cyano{3-[(3-methoxypropyl)amino]cyclohex-2-en-1-ylidene}ethanoate (25) in its E/E and/or E/Z geometrical configuration.

The E/Z form has the following structure:

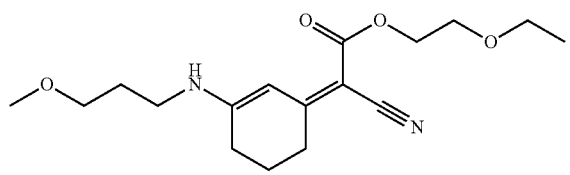 [SMILES: CCOCCOC(=O)/C(C#N)=C1\C=C(NCCCOC)CCC1]

The E/E form has the following structure:

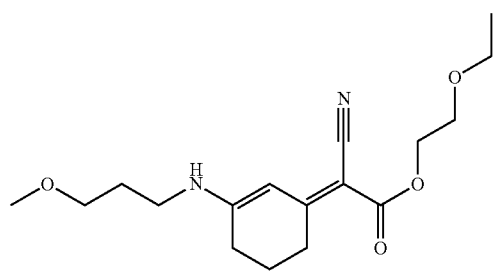 [SMILES: CCOCCOC(=O)/C(C#N)=C1/C=C(NCCCOC)CCC1]

The merocyanines in accordance with the invention may be present in the compositions according to the invention in a concentration ranging from 0.1% to 10% by weight, and preferentially from 0.2% to 5% by weight relative to the total weight of the composition.

The compounds of formulae (1) and (2) and in particular of formula (3) can be prepared according to known processes, as described for example in J. Org. Chem. USSR (English Translation) 26(8), p. 1562f (1990); J. Heterocycl. Chem. 33(3), p. 763-766 (1996); Khimiya Geterotsiklicheskikh Soedinenii 11, p. 1537-1543 (1984); Khimiya Geterotsiklicheskikh Soedinenii 3, p. 397-404 (1982); Chem. Heterocycl. Comp. (English Translation) 24(8), 914-919 (1988) and in Synthetic Communications Vol. 33, No. 3, 2003, p 367-371.

The synthesis of the compounds used in the present invention is also described in US 2003/0181483A1, WO 0234710, Eur. J. Org. Chem. 2003, 2250-2253, J. Med. Chem. 1996, 39, 1112-1124 and J. Org. Chem., Vol. 37, No. 8, 1972, 1141-1145 as follows:

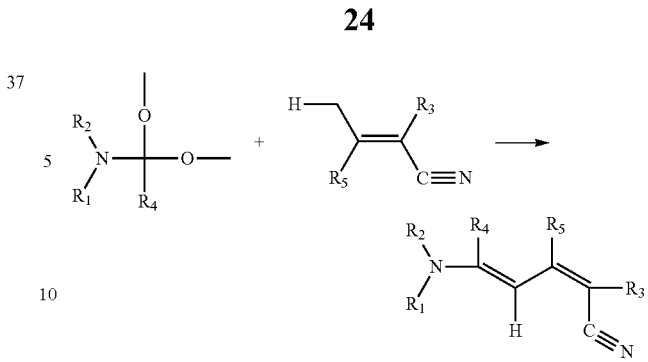

CH-acid vinylogen compounds are reacted with amide acetals.

In document J. Heterocyclic Chem., 27, 1990, 1143-1151 aminoacrylic acid esters or aminoacrylnitriles are reacted with ethoxymethylenecyanoacetates in ethanol so as to form the corresponding compounds of the present invention.

The compounds of formula (1) or (2) wherein, on the one hand, $R_4$ and $R_5$ or, on the other hand, $R_9$ and $R_{10}$ together form a carbocyclic ring containing 6 carbon atoms, respectively, can be prepared according to the protocols described in Pat. Appl. WO 2007/071582, in IP.com Journal (2009), 9(5A), 29-30 IPCOM000182396D under the title "Process for producing 3-amino-2-cyclohexan-1-ylidene compounds" and in U.S. Pat. No. 4,749,643 in col, 13, line 66-col. 14, line 57 and the references cited in this regard.

N-Substituted Amides

The amides in accordance with the invention are preferably chosen from the compounds of formula (4) below:

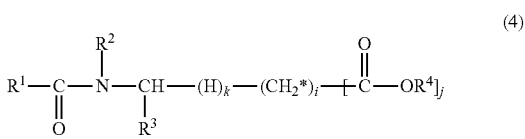

(4)

in which:
 the $R^1$ radical represents a saturated or unsaturated, aliphatic, cycloaliphatic or cyclic, optionally functionalized, monovalent hydrocarbon-based radical containing from 1 to 8 carbon atoms, preferably from 1 to 4 carbon atoms, limits included;
 the $R^2$, $R^3$ and $R^4$ radicals, which may be identical or different, represent saturated or unsaturated, aliphatic, cycloaliphatic or cyclic, optionally functionalized, monovalent hydrocarbon-based radicals containing from 1 to 30 carbon atoms, preferably from 1 to 22 carbon atoms, limits included;
 k is 0 or 1;
 i is an integer from 0 to 2;
 j is 0 or 1;
 with the proviso that:
 when j=1 then k is 0 and when j=0 then i=0 and k=1 and $R^1$ represents an unsaturated cyclic hydrocarbon-based radical, for example an aryl radical such as phenyl or naphthyl, which is optionally substituted, in particular with alkyls, for instance the tolyl radical, or an amide of formula (4) in which:
 $R^1$ represents a linear or branched $C_1$-$C_4$ alkyl radical; a linear or branched $C_2$-$C_4$ alkenyl radical, or an aryl radical;
 $R^2$ represents a hydrogen atom or a linear or branched $C_1$-$C_6$ alkyl group;

$R^3$ represents a hydrogen atom or a linear or branched $C_1$-$C_6$ alkyl group;

$R^4$ represents a linear or branched $C_1$-$C_{10}$ alkyl radical, a linear or branched $C_2$-$C_{10}$ alkenyl radical or a sterol residue;

with the proviso that:

when j=1 then k is 0 and when j=0 then i=0 and k=1 and $R^1$ represents an unsaturated cyclic hydrocarbon-based radical, for example an aryl radical such as phenyl or naphthyl, which is optionally substituted, in particular with alkyls, for instance the tolyl radical.

As examples of aliphatic saturated hydrocarbon-based radicals, mention may particularly be made of linear or branched, substituted or unsubstituted $C_1$-$C_{30}$, preferably $C_1$-$C_{22}$, alkyl radicals, and in particular methyl, ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

By way of examples of saturated cyclic hydrocarbon-based radicals, mention may particularly be made of cyclopentyl and cyclohexyl radicals, which are optionally substituted, in particular with alkyl radicals.

As examples of unsaturated aliphatic hydrocarbon-based radicals, mention may particularly be made of linear or branched, substituted or unsubstituted $C_2$-$C_{30}$, preferably $C_2$-$C_{22}$, alkenyl or alkynyl radicals, and in particular vinyl, allyl, oleyl and linoleyl radicals.

As examples of unsaturated cyclic hydrocarbon-based radicals, mention may particularly be made of aryl radicals such as phenyl and naphthyl, which are optionally substituted, in particular with alkyls, for instance the tolyl radical, and by way of examples of unsaturated cycloaliphatic radicals, mention may more particularly be made of benzyl and phenylethyl radicals.

The term "functionalized radicals" is intended to be more particularly radicals comprising in their chemical structure, both in the main chain and on a secondary link, one or more functional groups in particular of the ester, ether, alcohol, amine, amide and ketone type, but preferably ester-type.

The preferential amides of formula (4) are chosen from those wherein:

$R^1$ represents a linear or branched $C_1$-$C_4$ alkyl radical; a linear or branched $C_2$-$C_4$ alkenyl radical, or an aryl or benzyl radical, such as tolyl, phenyl or xylyl;

$R^2$ represents a hydrogen atom or a linear or branched $C_1$-$C_6$ alkyl group, preferably a linear or branched $C_1$-$C_6$ alkyl group;

$R^3$ represents a hydrogen atom or a linear or branched $C_1$-$C_6$ alkyl group;

$R^4$ represents a linear or branched $C_1$-$C_{10}$ alkyl radical, a linear or branched $C_2$-$C_{10}$ alkenyl radical or a sterol residue.

In formula (4) presented above, the $R^1$(CO)— group is an acyl group of an acid preferably chosen from the group made up of acetic acid, toluic acid and capric acid. These acids may also contain a hydroxyl group.

In formula (4) when j is 1, the —N($R^2$)CH($R^3$)($CH_2$)q (CO)— part of the amino acid ester is preferably chosen from those corresponding to the following amino acids: glycine, alanine, valine, leucine, isoleucine, serine, threonine, proline, hydroxyproline, β-alanine, N-butyl-β-alanine, aminobutyric acid, aminocaproic acid, sarcosine or N-methyl-β-alanine.

In formula (4), when j is 1, the part of the amino acid esters corresponding to the group $OR^4$ may be obtained from alcohols chosen from the group formed by methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol alcohol and isostearyl alcohol.

The amides of formula (4) in accordance with the invention are known per se. Some are in particular described with the methods for preparing them in patent applications EP 1 044 676 and EP 0 928 608 by the company Ajinomoto Co.

Others are known in the cosmetics industry as being insect repellent, such as N-acetyl N-butylaminopropionate or N,N-diethyltoluamide.

Among the compounds of formula (4) that are particularly preferred, mention may be made of:

N-acetyl N-butylaminopropionate having the formula below:

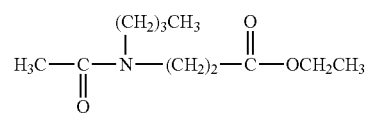

such as the product sold under the trade name Repellent R3535 by the company Merck;

and

N,N-diethyltoluamide having the formula:

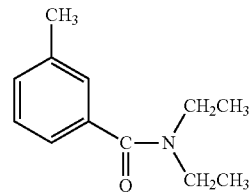

such as the product sold under the trade name DEET by the company Showa Denko.

The amides as defined previously are present in the compositions according to the invention in concentrations preferably ranging from 0.1% to 95% by weight, more particularly from 0.5% to 50% by weight and more preferentially from 1% to 20% by weight, relative to the total weight of the composition.

Oily Phase

The compositions in accordance with the invention comprise at least one oily phase.

For the purposes of the invention, the term "oily phase" is intended to mean a phase comprising at least one oil and all of the liposoluble and lipophilic ingredients and the fatty substances used for the formulation of the compositions of the invention.

The term "oil" is intended to mean any fatty substance that is in liquid form at ambient temperature (20-25° C.) and atmospheric pressure (760 mmHg).

The oily phase may comprise, in addition to the merocyanine screening agent(s) and optionally the lipophilic additional screening agents and the N,N-disubstituted amide(s) according to the invention, at least one volatile or non-volatile hydrocarbon-based oil and/or one volatile and/or non-volatile silicone oil and/or one volatile and/or non-volatile fluoro oil.

For the purposes of the present invention, the term "silicone oil" is intended to mean an oil comprising at least one silicon atom, and in particular at least one Si—O group.

The term "hydrocarbon-based oil" is intended to mean an oil mainly containing hydrogen and carbon atoms and optionally one or more heteroatoms, in particular nitrogen and oxygen. Thus, these oils may in particular contain one or more, carboxy, ester, ether, hydroxyl functions.

The term "fluoro oil" is intended to mean an oil comprising at least one fluorine atom.

For the purposes of the invention, the term "volatile oil" is intended to mean an oil that is capable of evaporating on contact with the skin or the keratin fibre in less than one hour, at ambient temperature and atmospheric pressure. The volatile oil(s) of the invention are volatile cosmetic oils which are liquid at ambient temperature and which have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" is intended to mean an oil that remains on the skin or the keratin fibre at ambient temperature and atmospheric pressure for at least several hours, and that in particular has a vapour pressure of less than $10^{-3}$ mmHg (0.13 Pa).

Hydrocarbon-Based Oils

Mention may in particular be made, as non-volatile hydrocarbon-based oils which can be used according to the invention, of:
(i) hydrocarbon-based oils of plant origin, such as glyceride triesters, which are generally triesters of fatty acids and of glycerol, the fatty acids of which can have varied chain lengths from $C_4$ to $O_{24}$, it being possible for these chains to be saturated or unsaturated and linear or branched; these oils are in particular wheatgerm oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passionflower oil and musk rose oil; or also caprylic/capric acid triglycerides, such as those sold by Stéarineries Dubois or those sold under the names Miglyol 810®, 812® and 818® by Dynamit Nobel;
(ii) synthetic ethers having from 10 to 40 carbon atoms;
(iii) linear or branched hydrocarbons of mineral or synthetic origin, such as petroleum jelly, polydecenes, hydrogenated polyisobutene, such as Parleam, squalane and mixtures thereof;
(iv) synthetic esters, for instance oils of formula RCOOR' in which R represents a linear or branched fatty acid residue containing from 1 to 40 carbon atoms and R' represents a hydrocarbon-based chain that is in particular branched, containing from 1 to 40 carbon atoms, on condition that R+R' is ≥10, for instance purcellin oil (cetostearyl octanoate), isopropyl myristate, isopropyl palmitate, $C_{12}$-$C_{15}$ alkyl benzoate, such as the product sold under the trade name Finsolv TN® or Witconol TN® by the company Witco or Tegosoft TN® by the company Evonik Goldschmidt, 2-ethylphenyl benzoate, such as the commercial product sold under the name X-Tend 226® by the company ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name Dub Dis by the company Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by the company Enichem Augusta Industriale, and also di(linear $C_{14}$-$C_{15}$ alkyl) tartrates, such as those sold under the name Cosmacol ETL® by the same company; or acetates;
(v) fatty alcohols which are liquid at ambient temperature and which have a branched and/or unsaturated carbon chain comprising from 12 to 26 carbon atoms, such as octyldodecanol, isostearyl alcohol, oleyl alcohol, 2-hexyldecanol, 2-butyloctanol or 2-undecylpentadecanol;
(vi) $C_{12}$-$C_{22}$ higher fatty acids, such as oleic acid, linoleic acid or linolenic acid;
(vii) carbonates, such as dicaprylyl carbonate, such as the product sold under the name Cetiol CC® by the company Cognis;
and mixtures thereof.

Among the non-volatile hydrocarbon-based oils that may be used according to the invention, preference will be given more particularly to glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, in particular octyldodecanol.

As volatile hydrocarbon-based oils that may be used according to the invention, mention may be made in particular of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4, 4,6-pentamethylheptane), isodecane or isohexadecane, the oils sold under the Isopar or Permethyl trade names, branched $C_8$-$C_{16}$ esters, isohexyl neopentanoate, and mixtures thereof.

Mention may also be made of the alkanes described in the Cognis patent applications WO 2007/068 371 or WO 2008/155 059 (mixtures of distinct alkanes differing by at least one carbon). These alkanes are obtained from fatty alcohols, which are themselves obtained from coconut or palm oil. Mention may be made of the mixtures of n-undecane ($C_{11}$) and n-tridecane ($C_{13}$) obtained in Examples 1 and 2 of patent application WO 2008/155 059 from the company Cognis. Mention may also be made of n-dodecane ($C_{12}$) and n-tetradecane ($C_{14}$) sold by Sasol under the respective references Parafol 12-97 and Parafol 14-97®, and also mixtures thereof.

Other volatile hydrocarbon-based oils, for instance petroleum distillates, in particular those sold under the name Shell Solt® by the company Shell, may also be used. According to one embodiment, the volatile solvent is chosen from volatile hydrocarbon oils having from 8 to 16 carbon atoms and mixtures thereof.

b) Silicone Oils

The non-volatile silicone oils can be chosen in particular from non-volatile polydimethylsiloxanes (PDMSs), polydimethylsiloxanes comprising alkyl or alkoxy groups which are pendent and/or at the end of the silicone chain, which groups each have from 2 to 24 carbon atoms, or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Examples of volatile silicone oils that may be mentioned include volatile linear or cyclic silicone oils, in particular those with a viscosity ≤8 centistokes ($8 \times 10^{-6}$ $m^2/s$) and in particular having from 2 to 7 silicon atoms, these silicones optionally comprising alkyl or alkoxy groups having from 1 to 10 carbon atoms. As volatile silicone oils that may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general formula (I):

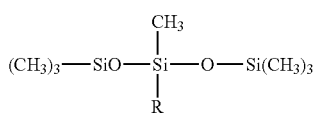

where R represents an alkyl group comprising from 2 to 4 carbon atoms, one or more hydrogen atoms of which may be replaced with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Fluoro Oils

Use may also be made of volatile fluoro oils, such as nonafluoromethoxybutane, decafluoropentane, tetradecafluorohexane, dodecafluoropentane, and mixtures thereof.

An oily phase according to the invention may also comprise other fatty substances, mixed with or dissolved in the oil.

Another fatty substance that may be present in the oily phase may be, for example:
- a fatty acid chosen from fatty acids comprising from 8 to 30 carbon atoms, such as stearic acid, lauric acid, palmitic acid and oleic acid;
- a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;
- a gum chosen from silicone gums (dimethiconol);
- a pasty compound, such as polymeric or non-polymeric silicone compounds, esters of a glycerol oligomer, arachidyl propionate, fatty acid triglycerides and derivatives thereof;
- and mixtures thereof.

Preferentially, the overall oily phase, including all the lipophilic substances of the composition capable of being dissolved in this same phase, represents from 5% to 95% by weight and preferentially from 10% to 80% by weight, relative to the total weight of the composition.

Aqueous Phase

The compositions according to the invention may also comprise at least one aqueous phase.

The aqueous phase contains water and optionally other water-soluble or water-miscible organic solvents.

An aqueous phase that is suitable for use in the invention may comprise, for example, a water chosen from a natural spring water, such as water from La Roche-Posay, water from Vittel or waters from Vichy, or a floral water.

The water-soluble or water-miscible solvents that are suitable for use in the invention comprise short-chain monoalcohols, for example $C_1$-$C_4$ monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may more particularly be made of ethanol, propylene glycol, glycerol, and mixtures thereof.

According to one particular form of the invention, the overall aqueous phase, including all the hydrophilic substances of the composition capable of being dissolved in this same phase, represents from 5% to 95% by weight and preferentially from 10% to 80% by weight, relative to the total weight of the composition.

Additives a) Additional UV-Screening Agents:

The compositions according to the invention may also contain one or more additional UV-screening agents chosen from hydrophilic, lipophilic or insoluble organic UV-screening agents and/or one or more mineral pigments. It will preferentially be constituted of at least one hydrophilic, lipophilic or insoluble organic UV-screening agent.

The term "hydrophilic UV-screening agent" is intended to mean any cosmetic or dermatological organic or inorganic compound for screening out UV radiation, which can be fully dissolved in molecular form in a liquid aqueous phase or which can be dissolved in colloidal form (for example in micellar form) in a liquid aqueous phase.

The term "lipophilic screening agent" is intended to mean any cosmetic or dermatological organic or inorganic compound for screening out UV radiation, which can be fully dissolved in molecular form in a liquid fatty phase or which can be dissolved in colloidal form (for example in micellar form) in a liquid fatty phase.

The term "insoluble UV-screening agent" is intended to mean any cosmetic or dermatological organic or inorganic compound for screening out UV radiation which has a solubility in water of less than 0.5% by weight and a solubility of less than 0.5% by weight in the majority of organic solvents such as liquid paraffin, fatty alcohol benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to ambient temperature. It may be readily evaluated in the laboratory.

The additional organic UV-screening agents are chosen in particular from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, in particular those cited in patent U.S. Pat. No. 5,624,663; benzimidazole derivatives; imidazoline compounds; bis-benzazolyl compounds, as described in patents EP 669 323 and U.S. Pat. No. 2,463,264; p-aminobenzoic acid (PABA) compounds; methylenebis(hydroxyphenylbenzotriazole) compounds, as described in patent applications U.S. Pat. Nos. 5,237,071, 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in patent application WO 93/04665; α-alkylstyrene-based dimers, such as those described in patent application DE 198

55 649; 4,4-diarylbutadiene compounds, as described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Cinnamic Compounds:

Ethylhexyl methoxycinnamate sold in particular under the trade name Parsol MCX® by DSM Nutritional Products, Isopropyl methoxycinnamate, Isoamyl p-methoxycinnamate sold under the trade name Neo Heliopan E 1000® by Symrise, DEA methoxycinnamate, Diisopropyl methyl cinnamate, Glyceryl Ethylhexanoate Dimethoxycinnamate.

Dibenzoylmethane Compounds:

Butylmethoxydibenzoylmethane, sold in particular under the trade name Parsol 1789® by DSM Nutritional Products, Isopropyldibenzoylmethane.

Para-Aminobenzoic Compounds:

PABA,

Ethyl PABA,

Ethyl dihydroxypropyl PABA,

Ethylhexyl dimethyl PABA, sold in particular under the name Escalol 507® by ISP, Glyceryl PABA, PEG-25 PABA, sold under the name Uvinul P 25® by BASF.

Salicylic Compounds:

Homosalate, sold under the name Eusolex HMS® by Rona/EM Industries,

Ethylhexyl salicylate, sold under the name Neo Heliopan OS® by Symrise,

Dipropylene glycol salicylate, sold under the name Dipsal® by Scher,

TEA salicylate, sold under the name Neo Heliopan TS® by Symrise.

β,β-Diphenylacrylate Compounds:

Octocrylene, sold in particular under the trade name Uvinul N 539® by BASF,

Etocrylene, sold in particular under the trade name Uvinul N 35® by BASF.

Benzophenone Compounds:

Benzophenone-1, sold under the trade name Uvinul 400® by BASF,

Benzophenone-2, sold under the trade name Uvinul D 50® by BASF,

Benzophenone-3 or Oxybenzone, sold under the trade name Uvinul M 40® by BASF,

Benzophenone-4, sold under the trade name Uvinul MS 40® by BASF,

Benzophenone-5,

Benzophenone-6, sold under the trade name Helisorb 11® by Norquay,

Benzophenone-8, sold under the trade name Spectra-Sorb UV-24® by American Cyanamid, Benzophenone-9, sold under the trade name Uvinul DS 49® by BASF, Benzophenone-12, n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by BASF, 1,1'-(1,4-Piperazinediyl)bis[1-[2-[4-(diethylamino)-2-hydroxybenzoyl]phenyl]methanone] (CAS 919803-06-8), such as described in patent application WO 2007/071 584; this compound advantageously being used in micronized form (average size of 0.02 to 2 µm), which may be obtained, for example, according to the micronization process described in patent applications GB-A-2 303 549 and EP-A-893 119, and in particular in the form of an aqueous dispersion.

Benzylidenecamphor Compounds:

3-Benzylidenecamphor, manufactured under the name Mexoryl SD® by Chimex,

4-Methylbenzylidenecamphor, sold under the name Eusolex 6300® by Merck,

Benzylidenecamphorsulfonic acid, manufactured under the name Mexoryl SL® by Chimex, Camphor benzalkonium methosulfate, manufactured under the name Mexoryl SO® by Chimex, Terephthalylidenedicamphorsulfonic acid, manufactured under the name Mexoryl SX® by Chimex, Polyacrylamidomethylbenzylidenecamphor, manufactured under the name Mexoryl SW® by Chimex.

Phenylbenzimidazole Compounds:

Phenylbenzimidazolesulfonic acid, sold in particular under the trade name Eusolex 232® by Merck.

Bis-Benzazolyl Compounds:

Disodium phenyl dibenzimidazole tetrasulfonate sold under the trade name Neo Heliopan AP® by Haarmann and Reimer.

Phenylbenzotriazole Compounds:

Drometrizole trisiloxane, sold under the name Silatrizole® by Rhodia Chimie.

Methylenebis(Hydroxyphenylbenzotriazole) Compounds:

Methylenebis(benzotriazolyl)tetramethylbutylphenol, in particular in solid form, such as the product sold under the trade name Mixxim BB/100® by Fairmount Chemical, or in the form of an aqueous dispersion of micronized particles with an average particle size ranging from 0.01 to 5 µm, more preferentially from 0.01 to 2 µm and more particularly from 0.020 to 2 µm, with at least one alkylpolyglycoside surfactant having the structure $C_nH_{2n+1}O(C_6H_{10}O_5)_xH$, in which n is an integer from 8 to 16 and x is the mean degree of polymerization of the $(C_6H_{10}O_5)$ unit and ranges from 1.4 to 1.6, as described in patent GB-A-2 303 549, sold in particular under the trade name Tinosorb M® by BASF, or in the form of an aqueous dispersion of micronized particles with an average particle size ranging from 0.02 to 2 µm, more preferentially from 0.01 to 1.5 µm and more particularly from 0.02 to 1 µm, in the presence of at least one polyglyceryl mono($C_8$-$C_{20}$)alkyl ester with a degree of glycerol polymerization of at least 5, such as the aqueous dispersions described in patent application WO 2009/063 392.

Triazine Compounds:

Bis-Ethylhexyloxyphenol methoxyphenyl triazine, sold under the trade name Tinosorb S® by BASF, Ethylhexyltriazone sold in particular under the trade name Uvinul T 150® by BASF, Diethylhexyl butamido triazone, sold under the trade name Uvasorb HEB® by Sigma 3V, 2,4,6-tris(dineopentyl 4'-aminobenzalmalonate)-s-triazine, 2,4,6-tris(diisobutyl 4'-aminobenzalmalonate)-s-triazine, 2,4-bis(n-butyl 4'-aminobenzoate)-6-(aminopropyltrisiloxane)-s-triazine, 2,4-bis(dineopentyl 4'-aminobenzalmalonate)-6-(n-butyl 4'-aminobenzoate)-s-triazine, symmetrical triazine screening agents substituted with naphthalenyl groups or polyphenyl groups described in patent U.S. Pat. No. 6,225,467, patent application WO 2004/085 412 (see compounds 6 and 9) or the document "Symmetrical Triazine Derivatives", IP.COM IPCOM000031257 Journal, INC West Henrietta, N.Y., US (20 Sep. 2004), in particular 2,4,6-tris(diphenyl) triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 µm), which may be obtained, for example, according to the micronization process described in patent applications GB-A-2 303 549 and EP-A-893 119, and in particular in aqueous dispersion form, silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy] disiloxanyl}propyl)amino]-s-triazine.

Anthranilic Compounds:

Menthyl anthranilate, sold under the trade name Neo Heliopan MA® by Symrise.

Imidazoline Compounds:

Ethylhexyl dimethoxybenzylidene dioxoimidazoline propionate.

Benzalmalonate Compounds:

Polyorganosiloxane comprising benzalmalonate functions, such as Polysilicone-15, sold under the trade name Parsol SLXO by Hoffmann-LaRoche.

4,4-Diarylbutadiene Compounds:

1,1-Dicarboxy(2,2'-dimethylpropyl)-4,4-diphenylbutadiene.

Benzoxazole Compounds:

2,4-bis[5-(1-dimethylpropyl)benzoxazol-2-yl(4-phenyl) imino]-6-(2-ethylhexyl)imino-1,3,5-triazine, sold under the name Uvasorb K2A® by Sigma 3V.

The preferential organic screening agents are chosen from:

Ethylhexyl methoxycinnamate
Ethylhexyl salicylate,
Homosalate,
Butyl methoxydibenzoylmethane
octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidenedicamphorsulfonic acid,
Disodium phenyl dibenzimidazole tetrasulfonate,
Methylenebis(benzotriazolyl)tetramethylbutylphenol,
bis-Ethylhexyloxyphenol methoxyphenyl triazine,
Ethylhexyl triazone
Diethylhexyl butamido triazone,
2,4,6-tris(dineopentyl 4'-aminobenzalmalonate)-s-triazine,
2,4,6-tris(diisobutyl 4'-aminobenzalmalonate)-s-triazine,
2,4-bis(n-butyl 4'-aminobenzoate)-6-(aminopropyltrisiloxane)-s-triazine,
2,4-bis(dineopentyl 4'-aminobenzalmalonate)-6-(n-butyl 4'-aminobenzoate)-s-triazine,
2,4-bis(n-butyl 4'-aminobenzalmalonate)-6-[(3-{1,3,3,3-tetramethyl-1-[(trimethylsilyl)oxy]disiloxanyl}propyl) amino]-s-triazine,
2,4,6-tris(diphenyl)triazine,
2,4,6-tris(terphenyl)triazine,
Drometrizole trisiloxane,
Polysilicone-15,
1,1-Dicarboxy(2,2'-dimethylpropyl)-4,4-diphenylbutadiene,
2,4-bis[5-(1-Dimethylpropyl)benzoxazol-2-yl-(4-phenyl) imino]-6-(2-ethylhexyl)imino-1,3,5-triazine,
and mixtures thereof.

The particularly preferred organic screening agents are chosen from:

Ethylhexyl salicylate,
Homosalate,
Butyl methoxydibenzoylmethane
octocrylene,
n-Hexyl 2-(4-diethylamino-2-hydroxybenzoyl)benzoate,
Terephthalylidenedicamphorsulfonic acid,
bis-Ethylhexyloxyphenol methoxyphenyl triazine,
Ethylhexyl triazone,
Diethylhexyl butamido triazone,
2,4-bis(n-butyl 4'-aminobenzalmalonate)-6-[(3-{1,3,3,3-tetramethyl-1-[(trimethylsilyl)oxy]disiloxanyl}propyl) amino]-s-triazine,
Drometrizole trisiloxane,
and mixtures thereof.

The inorganic UV-screening agents used in accordance with the present invention are metal oxide pigments. More preferentially, the inorganic UV-screening agents of the invention are metal oxide particles with a mean elementary particle size of less than or equal to 0.5 µm, more preferentially between 0.005 and 0.5 µm, even more preferentially between 0.01 and 0.2 µm, better still between 0.01 and 0.1 µm and more particularly between 0.015 and 0.05 µm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:

with silica, such as the product Sunveil® from the company Ikeda,
with silica and iron oxide, such as the product Sunveil F® from the company Ikeda,
with silica and alumina, such as the products Microtitanium Dioxide MT 500 SA® and Microtitanium Dioxide MT 100 SA from the company Tayca and Tioveil from the company Tioxide,
with alumina, such as the products Tipaque TTO-55 (B)® and Tipaque TTO-55 (A)® from the company Ishihara and UVT 14/4 from the company Sachtleben Pigments,
with alumina and aluminium stearate, such as the products Microtitanium Dioxide MT 100 T®, MT 100 TX®, MT 100 Z® and MT-01® from the company Tayca, the products Solaveil CT-10 W®, Solaveil XT-300® and Solaveil CT 1000 from the company Croda, the product Eusolex T-AVO® from the company Merck, and the product UV Titan M 160 from Sachtleben Pigments, with silica, alumina and alginic acid, such as the product MT-100 AQ® from the company Tayca, with alumina and aluminium laurate, such as the product Microtitanium Dioxide MT 100 S® from the company Tayca, with iron oxide and iron stearate, such as the product Microtitanium Dioxide MT 100 F® from the company Tayca, with zinc oxide and zinc stearate, such as the product BR 351® from the company Tayca, with silica and alumina and treated with a silicone, such as the products Microtitanium Dioxide MT 600 SAS®, Microtitanium Dioxide MT 500 SAS® or Microtitanium Dioxide MT 100 SAS® from the company Tayca, with silica, alumina and aluminium stearate and treated with a silicone, such as the product STT-30-DS® from the company Titan Kogyo, with silica and treated with a silicone, such as the product UV-Titan X 195® from the company Sachtleben Pigments, with alumina and treated with a silicone, such as the products Tipaque TTO-55 (S)® from the company Ishihara or UV Titan M 262® from the company Sachtleben Pigments, with triethanolamine, such as the product STT-65-S from the company Titan Kogyo, with stearic acid, such as the product Tipaque TTO-55 (C)® from the company Ishihara, with sodium hexametaphosphate, such as the product Microtitanium Dioxide MT 150 W® from the company Tayca, $TiO_2$ treated with octyltrimethylsilane, sold under the trade name T 805® by the company Degussa Silices, $TiO_2$ treated with a polydimethylsiloxane, sold under the trade name 70250 Cardre UF TiO2SI3® by the company Cardre, and UV Titan M 195 by Sachtleben Pigments, anatase/rutile $TiO_2$ treated with a polydimethylhydrogenosiloxane, sold under the trade name Microtitanium Dioxyde USP Grade Hydrophobic® by the company Color Techniques, $TiO_2$ coated with triethylhexanoin, with aluminium stearate and with alumina sold under the trade name Solaveil CT-200-LQ-(WD) by Croda, $TiO_2$ coated with aluminium stearate, with alumina and with silicone sold under the trade name Solaveil CT-12W-LQ-(WD) by Croda, $TiO_2$ coated with lauroyl lysine sold by Daito Kasei Kogyo under the name LL 5 Titanium Dioxyde CR 50, $TiO_2$ coated with C9-15 fluoroalcohol phosphate et with aluminium hydroxide sold by Daito Kasei Kogyo under the name PFX-5 TiO2 CR-50.

Mention may also be made of $TiO_2$ pigments doped with at least one transition metal such as iron, zinc or manganese and more particularly manganese. Preferably, said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG-3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of $TiO_2$ particles doped with manganese in capric/caprylic acid triglyceride in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wackherr under the name Transparent titanium oxide PW®, by the company Miyoshi Kasei under the name UFTRO, by the company Tomen under the name ITS® and by the company Tioxide under the name Tioveil AQ.

The uncoated zinc oxide pigments are for example:

those sold under the name Z-Cote by the company Sunsmart;

those sold under the name Nanox® by the company Elementis;

those sold under the name Nanogard WCD 2025® by the company Nanophase Technologies.

The coated zinc oxide pigments are for example:

those sold under the name Zinc Oxide CS-5® by the company Toshibi (ZnO coated with polymethylhydrogenosiloxane);

those sold under the name Nanogard Zinc Oxide FN® by the company Nanophase Technologies (as a 40% dispersion in Finsolv TN®, C12-C15 alkyl benzoate);

those sold under the name Daitopersion Zn-30® and Daitopersion Zn-50® by the company Daito (dispersions in cyclopolymethylsiloxane/oxyethylenated polydimethylsiloxane, containing 30% or 50% of zinc oxides coated with silica and polymethylhydrogenosiloxane);

those sold under the name NFD Ultrafine ZnO® by the company Daikin (ZnO coated with perfluoroalkyl phosphate and copolymer based on perfluoroalkylethyl as a dispersion in cyclopentasiloxane);

those sold under the name SPD-Z1® by the company Shin-Etsu (ZnO coated with silicone-grafted acrylic polymer, dispersed in cyclodimethylsiloxane);

those sold under the name Escalol Z100® by the company ISP (alumina-treated ZnO dispersed in the ethylhexyl methoxycinnamate/PVP-hexadecene copolymer/methicone mixture);

those sold under the name Fuji ZnO-SMS-100® by the company Fuji Pigment (ZnO coated with silica and polymethylsilsesquioxane);

those sold under the name Nanox Gel TN® by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company RhOne-Poulenc.

The uncoated iron oxide pigments are sold, for example, by the company Arnaud under the names Nanogard WCD 2002® (FE 45B®), Nanogard Iron FE 45 BL AQ, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008

(FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

The additional UV-screening agents according to the invention are preferably present in the compositions according to the invention in a content ranging from 0.1% to 60% by weight and in particular from 5% to 30% by weight relative to the total weight of the composition.

b) Other Additives:

The compositions in accordance with the present invention may also comprise conventional cosmetic adjuvants chosen in particular from organic solvents, ionic or nonionic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, basifying or acidifying agents or any other ingredient commonly used in the cosmetic and/or dermatological field.

Mention may be made, among organic solvents, of alcohols other than $C_1$-$C_4$ monoalkanols as defined above and in particular short-chain $C_2$-$C_8$ polyols, such as glycerol or diols, such as caprylyl glycol, 1,2-pentanediol, propanediol, butanediol, glycols and glycol ethers, such as ethylene glycol, propylene glycol, butylene glycol, dipropylene glycol or diethylene glycol.

Mention may be made, as thickeners, of carboxyvinyl polymers, such as the Carbopols® (Carbomers) and the Pemulens, such as Pemulen TR1® and Pemulen TR2® (acrylate/C10-C30 alkyl acrylate copolymer); polyacrylamides, for instance the crosslinked copolymers sold under the names Sepigel 305® (CTFA name: polyacrylamide/$C_{13-14}$ isoparaffin/Laureth 7) or Simulgel 600 (CTFA name: acrylamide/sodium acryloyldimethyl taurate copolymer/isohexadecane/polysorbate 80) by the company SEPPIC; 2-acrylamido-2-methylpropanesulfonic acid polymers and copolymers, optionally crosslinked and/or neutralized, such as the poly(2-acrylamido-2-methylpropanesulfonic acid) sold by the company Hoechst under the trade name Hostacerin AMPS® (CTFA name: ammonium polyacryloyldimethyl taurate) or Simulgel 800®, sold by the company SEPPIC (CTFA name: sodium polyacryloyldimethyl taurate/polysorbate 80/sorbitan oleate); copolymers of 2-acrylamido-2-methylpropanesulfonic acid and of hydroxyethyl acrylate, such as Simulgel NS® and Sepinov EMT 10®, sold by the company SEPPIC; cellulose derivatives, such as hydroxyethylcellulose; polysaccharides and in particular gums, such as xanthan gum; water-soluble or water-dispersible silicone derivatives, such as acrylic silicones, polyether silicones and cationic silicones, and mixtures thereof.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide or potassium hydroxide.

Preferably, the cosmetic composition comprises one or more basifying agents selected from alkanolamines, in particular triethanolamine, and sodium hydroxide.

In the case of a direct emulsion, the pH of the composition in accordance with the invention is generally between 3 and 12 approximately, preferably between 5 and 11 approximately and even more particularly from 6 to 8.5.

Among the active agents for caring for keratin materials such as the skin, the lips, the scalp, the hair, the eyelashes or the nails, examples that may be mentioned include:
- vitamins and derivatives or precursors thereof, alone or as mixtures;
- antioxidants;
- free-radical scavengers;
- antipollution agents;
- self-tanning agents;
- antiglycation agents;
- calmatives;
- deodorants;
- essential oils;
- NO-synthase inhibitors;
- agents for stimulating the synthesis of dermal or epidermal macromolecules and/or for preventing their degradation;
- agents for stimulating fibroblast proliferation;
- agents for stimulating keratinocyte proliferation;
- muscle relaxants;
- refreshing agents;
- tensioning agents,
- matting agents;
- depigmenting agents;
- pro-pigmenting agents;
- keratolytic agents;
- desquamating agents;
- moisturizers;
- anti-inflammatory agents;
- antimicrobial agents;
- slimming agents;
- agents that act on the energy metabolism of cells;
- insect repellents;
- substance P or CGRP antagonists;
- hair-loss counteractants;
- antiwrinkle agents;
- antiageing agents.

Those skilled in the art will select said active agent(s) according to the effect desired on the skin, the hair, the eyelashes, the eyebrows or the nails.

Of course, those skilled in the art will take care to choose the abovementioned optional additional compound or compounds and/or their amounts so that the advantageous properties intrinsically attached to the compositions in accordance with the invention are not, or not substantially, detrimentally affected by the envisaged addition or additions.

Presentation Forms

The compositions according to the invention may be prepared according to the techniques that are well known to those skilled in the art. They may in particular be in the form of a simple or complex emulsion (O/W, W/O, O/W/O or W/O/W), such as a cream, a milk or a cream gel.

They may also be in anhydrous form, for instance in the form of an oil. The term "anhydrous composition" is intended to mean a composition containing less than 1% by weight of water, or even less than 0.5% of water, and in particular free of water, the water not being added during the preparation of the composition but corresponding to the residual water provided by the mixed ingredients. They may optionally be packaged in aerosol form and may be in the form of a mousse or a spray.

In the case of compositions in the form of oil-in-water or water-in-oil emulsions, the emulsification processes that may be used are of the paddle or impeller, rotor-stator and HPH type.

In order to obtain stable emulsions with a low content of polymer (oil/polymer ratio >25), it is possible to prepare the dispersion in concentrated phase and then to dilute the dispersion with the remainder of the aqueous phase.

It is also possible, via HPH (between 50 and 800 bar), to obtain stable dispersions with drop sizes that may be as small as 100 nm.

The emulsions generally comprise at least one emulsifier chosen from amphoteric, anionic, cationic or nonionic emulsifiers, used alone or as a mixture. The emulsifiers are chosen in an appropriate manner according to the emulsion to be obtained (W/O or O/W emulsion).

Examples of W/O emulsifying surfactants that may be mentioned include alkyl esters or ethers of sorbitan, of glycerol, of polyol or of sugars; silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE 09® by the company Goldschmidt. One or more coemulsifiers, which may be chosen advantageously from the group comprising polyol alkyl esters, may also be added thereto.

Mention may also be made of non-silicone emulsifying surfactants, in particular alkyl esters or ethers of sorbitan, of glycerol, of polyol or of sugars.

Polyol alkyl esters that may in particular be mentioned include polyethylene glycol esters, for instance PEG-30 dipolyhydroxystearate, such as the product sold under the name Arlacel P135® by the company ICI.

Examples of glycerol and/or sorbitan esters that may be mentioned include polyglyceryl isostearate, such as the product sold under the name Isolan GI 34® by the company Goldschmidt; sorbitan isostearate, such as the product sold under the name Arlacel 987® by the company ICI; sorbitan isostearate and glycerol, such as the product sold under the name Arlacel 986® by the company ICI, and mixtures thereof.

For the O/W emulsions, examples of nonionic emulsifying surfactants that may be mentioned include polyoxyalkylenated (more particularly polyoxyethylenated and/or polyoxypropylenated) esters of fatty acids and of glycerol; oxyalkylenated esters of fatty acids and of sorbitan; polyoxyalkylenated (in particular polyoxyethylenated and/or polyoxypropylenated) esters of fatty acids, optionally in combination with an ester of fatty acid and of glycerol, such as the PEG-100 Stearate/Glyceryl Stearate mixture sold, for example, by the company ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000® and Plantaren 1200®, cetostearyl glucoside, optionally as a mixture with cetostearyl alcohol, sold, for example, under the name Montanov 68® by the company SEPPIC, under the name Tegocare CG900 by the company Goldschmidt and under the name Emulgade KE3302® by the company Henkel, and arachidyl glucoside, for example in the form of the mixture of arachidyl and behenyl alcohols and of arachidyl glucoside sold under the name Montanov 202® by the company SEPPIC. According to one particular embodiment of the invention, the mixture of the alkyl polyglucoside as defined above with the corresponding fatty alcohol can be in the form of a self-emulsifying composition, for example as disclosed in the document WO-A-92/06778.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, in particular cosmetic treatments, for the skin, the lips and the hair, including the scalp, in particular for protecting and/or caring for the skin, the lips and/or the hair, and/or for making up the skin and/or the lips.

Another subject of the present invention is constituted of the use of the compositions according to the invention as defined above for the manufacture of products for the cosmetic treatment of the skin, the lips, the nails, the hair, the eyelashes, the eyebrows and/or the scalp, in particular care products, sunscreen products and makeup products.

The cosmetic compositions according to the invention may be used, for example, as makeup products.

Another subject of the present invention is constituted of a non-therapeutic cosmetic process for caring for and/or making up a keratin material, which consists in applying, to the surface of said keratin material, at least one composition according to the invention as defined above.

The cosmetic compositions according to the invention may be used, for example, as care products and/or sunscreen products for the face and/or body with a liquid to semi-liquid consistency, such as milks, more or less smooth creams, cream gels or pastes. They may optionally be packaged in aerosol form and may be in the form of a mousse or a spray.

The compositions according to the invention in the form of vapourizable fluid lotions in accordance with the invention are applied to the skin or hair in the form of fine particles by means of pressurizing devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight, relative to the total weight of the composition.

Assembly

According to another aspect, the invention also relates to a cosmetic assembly comprising:

i) a container delimiting one or more compartment(s), said container being closed by a closing member and optionally being unsealed; and ii) a makeup and/or care composition in accordance with the invention placed inside said compartment(s).

The container can, for example, be in the form of a pot or a case.

The closing member can be in the form of a lid comprising a cap mounted so as to be able to move by translation or by pivoting relative to the container housing said makeup and/or care composition(s).

The examples that follow serve to illustrate the invention without, however, being limiting in nature. In these examples, the amounts of the composition ingredients are given as weight percentages relative to the total weight of the composition.

EXAMPLE A1: PREPARATION OF COMPOUND (14)

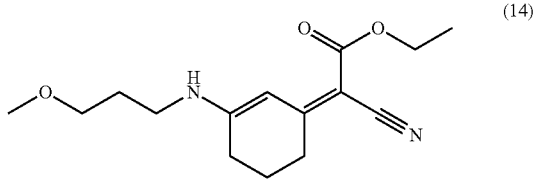 [SMILES: CCOC(=O)/C(C#N)=C1\C=C(NCCCOC)CCC1]

(14)

122.23 grams of 3-[(3-methoxypropyl)amino]-2-cyclohexen-1-one are alkylated with dimethyl sulfate or alternatively with diethyl sulfate and treated with 75.45 g of ethyl cyanoacetate in approximately equimolar proportions in the presence of a base and optionally of a solvent.

The following base/solvent combinations are used:

| Example | Base | Solvent |
|---|---|---|
| Example A1.1 | DBU (1,8-diazabicyclo[5.4.0] undec-7-ene) | dimethylacetamide |
| Example A1.2 | Triethylamine | isopropanol |
| Example A1.3 | 3-methoxypropylamine | isopropanol |
| Example A1.4 | 3-methoxypropylamine | tert-amylalcohol |
| Example A1.5 | 3-methoxypropylamine | toluene |
| Example A1.6 | 3-methoxypropylamine | dimethylformamide |
| Example A1.7 | 3-methoxypropylamine | no solvent |
| Example A1.8 | N-morpholine | isopropanol |

The completion of the alkylation reaction can be monitored for example by methods such as TLC, GC or HPLC.

162.30 g of compound (14) are obtained in the form of a brown oil. After crystallization, the product is obtained in the form of yellowish crystals.

Melting point: 92.7° C.

EXAMPLE A2: PREPARATION OF COMPOUND (15)

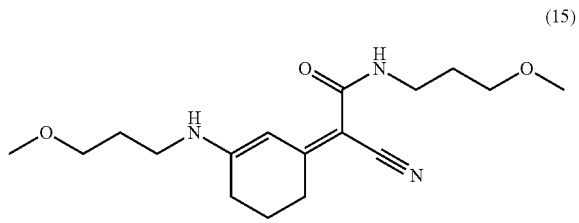

(15)

101.00 grams of 3-[(3-methoxypropyl)amino]-2-cyclohexen-1-one are alkylated with dimethyl sulfate or alternatively with diethyl sulfate and treated with 86.00 g of 2-cyano-N-(3-methoxypropyl)acetamide in approximately equimolar proportions in the presence of a base and optionally of a solvent. The following base/solvent combinations are used:

| Example | Base | Solvent |
|---|---|---|
| Example A2.1 | DBU (1,8-diazabicyclo[5.4.0] undec-7-ene) | dimethylacetamide |
| Example A2.2 | Triethylamine | isopropanol |
| Example A2.3 | 3-methoxypropylamine | isopropanol |
| Example A2.4 | 3-methoxypropylamine | tert-amylalcohol |
| Example A2.5 | 3-methoxypropylamine | toluene |
| Example A2.6 | 3-methoxypropylamine | dimethylformamide |
| Example A2.7 | 3-methoxypropylamine | no solvent |

The crude product (15) is obtained in the form of a dark brown oil.

After silica gel column chromatography (eluent: 99/1 toluene/methanol), 81.8 grams of product are obtained in the form of yellowish crystals.

Melting point: 84.7-85.3° C.

EXAMPLE A3: PREPARATION OF COMPOUND (27)

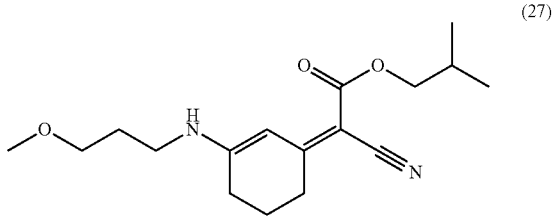 [SMILES: COCCCNC1=C/C(=C(/C#N)C(=O)OCC(C)C)CCC1]

(27)

13.09 grams of 3-[(3-methoxypropyl)amino]-2-cyclohexen-1-one are alkylated with dimethyl sulfate or alternatively with diethyl sulfate and treated with 10.12 g of isobutyl cyanoacetate in the presence of a base and optionally of a solvent. The following base/solvent combinations are used:

| Example | Base | Solvent |
|---|---|---|
| Example A3.1 | DBU (1,8-diazabicyclo[5.4.0]undec-7-ene) | dimethylacetamide |
| Example A3.2 | Triethylamine | isopropanol |
| Example A3.3 | 3-methoxypropylamine | isopropanol |
| Example A3.4 | N-methylmorpholine | tert-amylalcohol |
| Example A3.5 | 3-methoxypropylamine | toluene |
| Example A3.6 | 3-methoxypropylamine | dimethylformamide |
| Example A3.7 | 3-methoxypropylamine | no solvent |

15.97 grams of crude product (27) are obtained in the form of a dark brown oil.

After silica gel column chromatography (eluent: toluene/acetone), 13.46 grams of product are obtained in the form of yellowish crystals.

Melting point: 96.3° C.

EXAMPLE A4: PREPARATION OF COMPOUND (25)

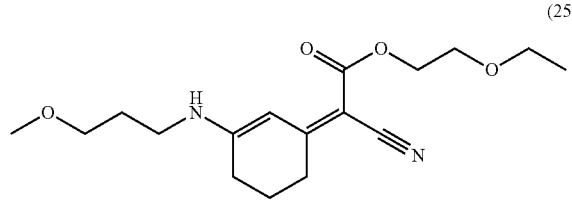

(25)

148.4 grams of 3-[(3-methoxypropyl)amino]-2-cyclohexen-1-one are alkylated with dimethyl sulfate or alternatively with diethyl sulfate and treated with 130.00 g of 2-ethoxyethyl cyanoacetate in the presence of an organic base and of a solvent.

The following base/solvent combinations are used:

| Example | Base | Solvent |
|---|---|---|
| Example A4.1 | DBU (1,8-diazabicyclo[5.4.0]undec-7-ene) | dimethylacetamide |
| Example A4.2 | Triethylamine | isopropanol |
| Example A4.3 | 3-methoxypropylamine | isopropanol |
| Example A4.4 | N-methylmorpholine | tert-amylalcohol |
| Example A4.5 | 3-methoxypropylamine | toluene |
| Example A4.6 | 3-methoxypropylamine | dimethylformamide |
| Example A4.7 | 3-methoxypropylamine | no solvent |

FORMULATION EXAMPLES

Protocol for Evaluating Solubility:

The solubility of the merocyanine in oily solutions is evaluated macroscopically and microscopically. It is considered that the merocyanine is soluble if, at ambient temperature, the solution appears to the eye to be clear and translucent, and it does not exhibit any visible crystals under a white-light or polarized-light microscope (objective ×20 to ×40). The solubility is evaluated at ambient temperature, on the day the solution is prepared and then over time. During this time period, the solutions are stored at ambient temperature and 4° C.

| Ingredients | Formulation 1 (invention) | Formulation 2 (outside the invention) |
|---|---|---|
| Compound (25) | 10 | 10 |
| Ethyl butyl acetylaminopropionate (Repellent R3535 from Merck) | 90 | — |
| Phenylethyl benzoate (and) benzoic acid (X-tend 226 ®-ISP) | — | 90 |
| Solubility at $t_0$ | soluble | soluble |
| Solubility at $t_{48\,h}$ | soluble | insoluble |
| Solubility at $t_{3\,Monthes}$ | soluble | insoluble |

EXAMPLES 3 ET 4

| Ingredients | Example 3 (outside the invention) | Exemple 4 (invention) |
|---|---|---|
| Compound (25) | 8.36 | 8.36 |
| DIETHYLAMINO HYDROXYBENZOYL HEXYL BENZOATE (UVINUL A PLUS from BASF) | 5.57 | 5.57 |
| ETHYLHEXYL TRIAZONE (UVINUL T 150 from BASF) | 11.14 | 11.14 |
| DROMETRIZOLE TRISILOXANE (SILATRIZOLE from RHODIA) | 22.28 | 22.28 |
| BIS-ETHYLHEXYLOXYPHENOL METHOXYPHENYL TRIAZINE (TINOSORB S from BASF) | 8.36 | 8.36 |
| PHENOXYETHANOL | 0.84 | 0.84 |
| CAPRYLYL GLYCOL | 1.67 | 1.67 |
| ISOPROPYL LAUROYL SARCOSINATE-(ELDEW 205 from AJINOMOTO) | 41.78 | |
| ETHYL BUTYLACETYLAMINO PROPIONATE-(Repellent R3535 from MERCK) | | 41.78 |
| Stability at ambient temperature | 2 days | >2 months (no recrystallization) |
| Stability at temperature of 4° C. | 2 days | >2 months (no recrystallization) |

Oil Preparation Method:

The compositions described in Examples 1 and 4 are prepared in the following way: the screening agents and the oil are introduced successively into a container, before being stirred by means of a magnetic stirrer and being heated at 90° C. between 10 min and 1 h, until the merocyanine has dissolved.

These results show that the amide compound according to the invention makes it possible to maintain the solubility of the merocyanine even in the presence of additional UV-screening agents.

The invention claimed is:
1. A cosmetic or dermatological composition comprising, in a physiologically acceptable medium:

a) at least one merocyanine chosen from the following compounds and also the E/E- or E/Z-geometrical isomer forms thereof:

TABLE A

| Compound | Structure |
|---|---|
| 1 | 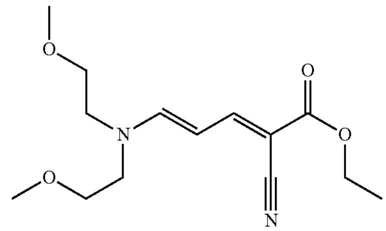 [SMILES: CCOC(=O)/C(C#N)=C/C=C/N(CCOC)CCOC] |
| 2 | 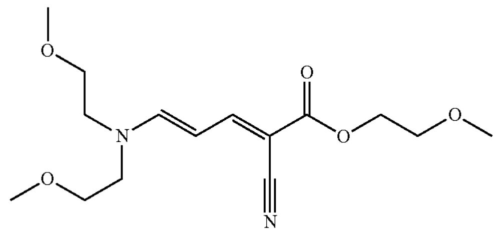 |
| 3 | 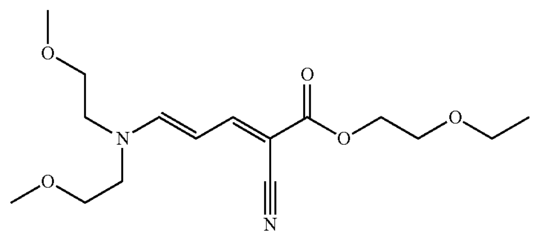 [SMILES: CCOCCOC(=O)/C(C#N)=C/C=C/N(CCOC)CCOC] |
| 4 | 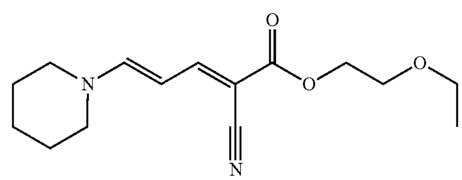 [SMILES: CCOCCOC(=O)/C(C#N)=C/C=C/N1CCCCC1] |
| 5 | 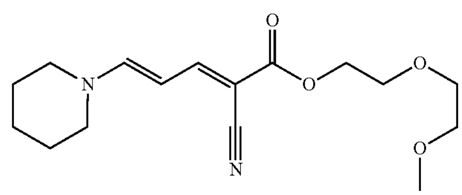 [SMILES: COCCOCCOC(=O)/C(C#N)=C/C=C/N1CCCCC1] |
| 6 | 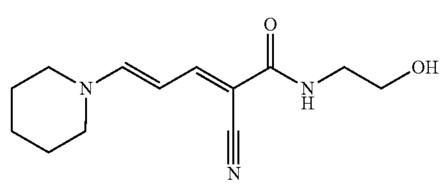 [SMILES: N#C/C(=C\C=C\N1CCCCC1)C(=O)NCCO] |
| 7 | 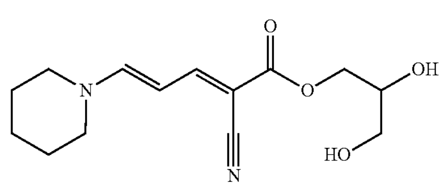 [SMILES: N#C/C(=C\C=C\N1CCCCC1)C(=O)OCC(O)CO] |

TABLE A-continued

| Compound | Structure |
|---|---|
| 8 | (piperidine-N-CH=CH-CH=C(CN)-C(=O)-O-CH2-CH(OH)-CH2-CH2-CH3) |
| 9 | (morpholine-N-CH=CH-CH=C(CN)-C(=O)-O-CH2-CH(OH)-CH2OH) |
| 10 | (morpholine-N-CH=CH-CH=C(CN)-C(=O)-O-CH2-CH2-O-CH2-CH3) |
| 11 | (dibutylamine-N-CH=CH-CH=C(CN)-C(=O)-O-CH2-CH(OH)-CH2OH) |
| 12 | (HO-CH2-CH2-N(butyl)-CH=CH-CH=C(CN)-C(=O)-O-butyl) |
| 13 | (bis(2-hydroxypropyl)amine-N-CH=CH-CH=C(CN)-C(=O)-O-hexyl) |
| 14 | (methoxypropyl-NH-cyclohexenyl=C(CN)-C(=O)-O-ethyl) |

TABLE A-continued

| Compound | Structure |
|---|---|
| 15 | 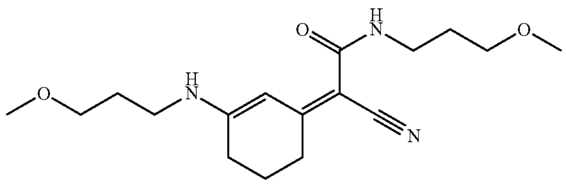 |
| 16 | 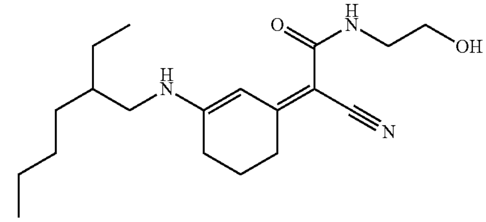 [SMILES: CCCCC(CC)CNC1=C/C(=C(/C#N)C(=O)NCCO)CCC1] |
| 17 | 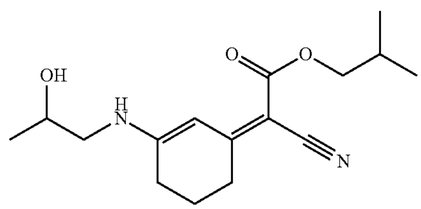 [SMILES: CC(C)COC(=O)/C(C#N)=C1\C=C(NCC(C)O)CCC1] |
| 18 | 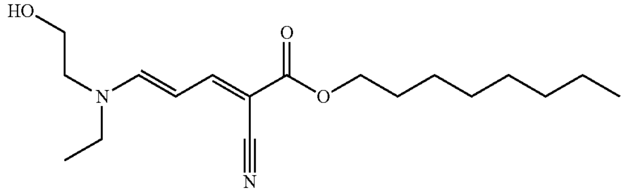 [SMILES: CCCCCCCCOC(=O)/C(C#N)=C/C=C/N(CC)CCO] |
| 19 | 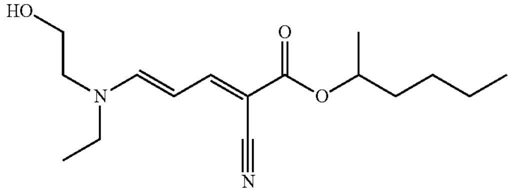 [SMILES: CCCCC(C)OC(=O)/C(C#N)=C/C=C/N(CC)CCO] |
| 20 | 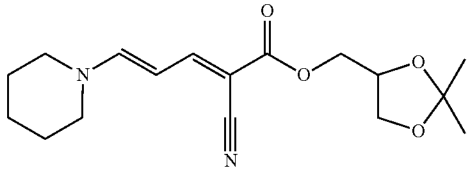 [SMILES: CC1(C)OCC(COC(=O)/C(C#N)=C/C=C/N2CCCCC2)O1] |
| 21 | 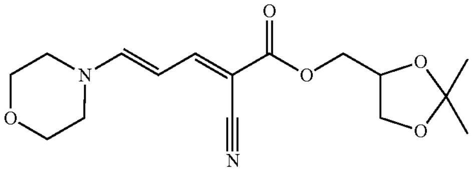 [SMILES: CC1(C)OCC(COC(=O)/C(C#N)=C/C=C/N2CCOCC2)O1] |
| 22 | 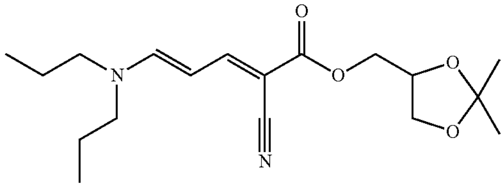 [SMILES: CCCN(/C=C/C=C(\C#N)C(=O)OCC1COC(C)(C)O1)CCC] |

TABLE A-continued

| Compound | Structure |
|---|---|
| 23 | 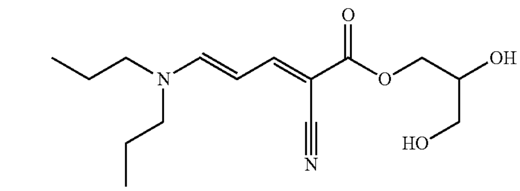 [SMILES: CCCN(/C=C/C=C(\C#N)C(=O)OCC(O)CO)CCC] |
| 24 | 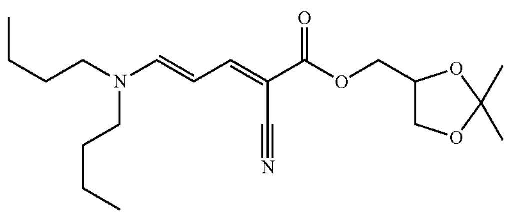 [SMILES: CCCCN(/C=C/C=C(\C#N)C(=O)OCC1COC(C)(C)O1)CCCC] |
| 25 | 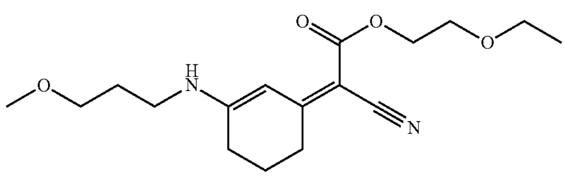 [SMILES: CCOCCOC(=O)/C(C#N)=C1\C=C(NCCCOC)CCC1] |
| 26 | 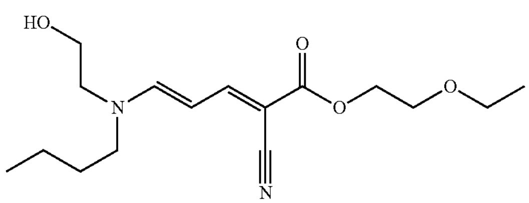 [SMILES: CCCCN(/C=C/C=C(\C#N)C(=O)OCCOCC)CCO] |
| 27 | 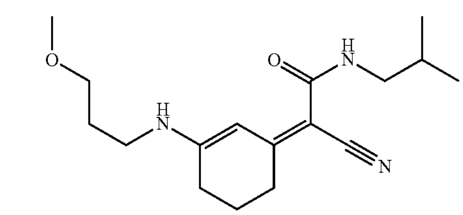 [SMILES: COCCCNC1=C/C(=C(/C#N)C(=O)NCC(C)C)CCC1] |
| 28 | 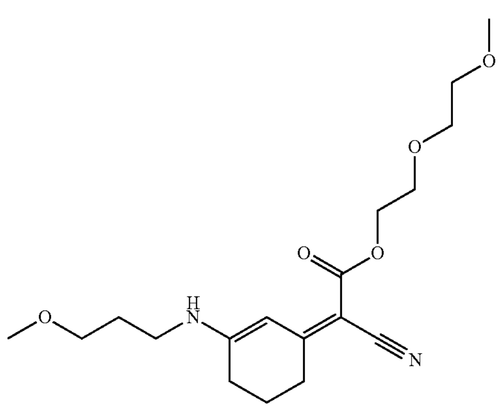 |

TABLE A-continued
| Compound | Structure |
|---|---|
| 29 | 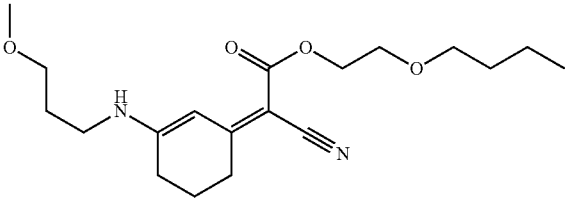 [SMILES: CCCCOCCOC(=O)/C(C#N)=C1\C=C(NCCCOC)CCC1] |
| 30 | 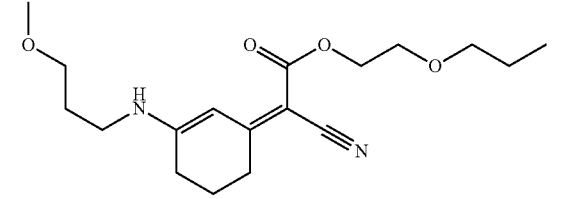 [SMILES: CCCOCCOC(=O)/C(C#N)=C1\C=C(NCCCOC)CCC1] |
| 31 | 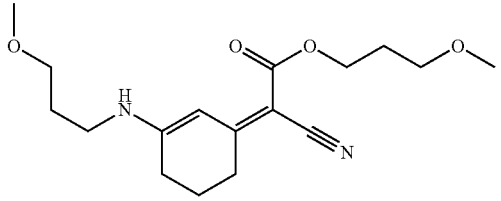 [SMILES: COCCCNC1=C/C(=C(/C#N)C(=O)OCCCOC)CCC1] |
| 32 | 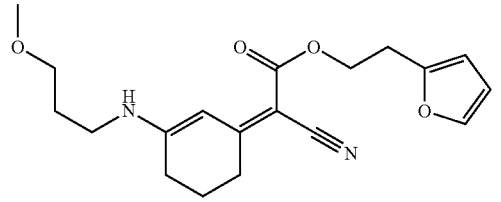 [SMILES: COCCCNC1=C/C(=C(/C#N)C(=O)OCCc2ccco2)CCC1] |
| 33 | 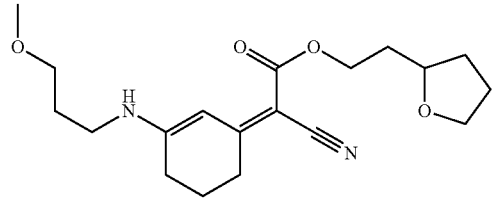 [SMILES: COCCCNC1=C/C(=C(/C#N)C(=O)OCCC2CCCO2)CCC1] |
| 34 | 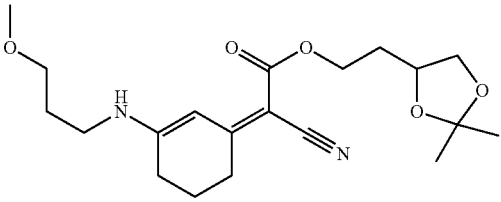 [SMILES: COCCCNC1=C/C(=C(/C#N)C(=O)OCCC2COC(C)(C)O2)CCC1] |
| 35 | 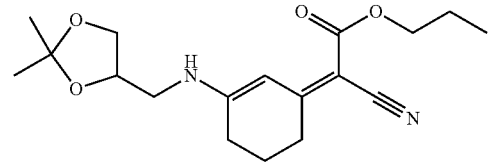 [SMILES: CCCOC(=O)/C(C#N)=C1\C=C(NCC2COC(C)(C)O2)CCC1] |

TABLE A-continued

| Compound | Structure |
|---|---|
| 36 | 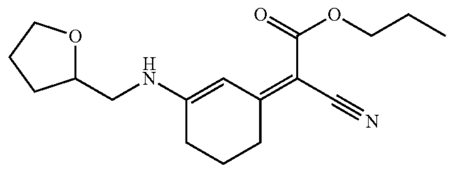 [SMILES: CCCOC(=O)/C(C#N)=C1\C=C(NCC2CCCO2)CCC1] |
| 37 | 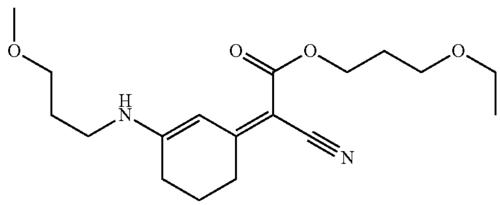 [SMILES: CCOCCCOC(=O)/C(C#N)=C1\C=C(NCCCOC)CCC1] |
| 38 | 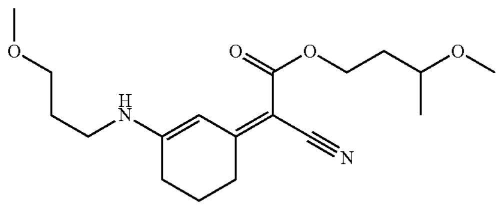 [SMILES: COCCCNC1=C/C(=C(/C#N)C(=O)OCCC(C)OC)CCC1] |
| 39 | 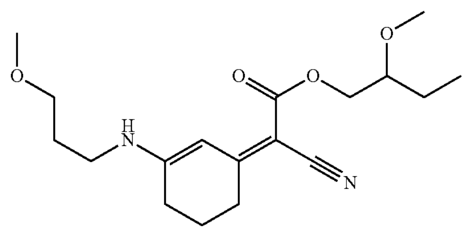 [SMILES: CCC(COC(=O)/C(C#N)=C1\C=C(NCCCOC)CCC1)OC] |
| 40 | 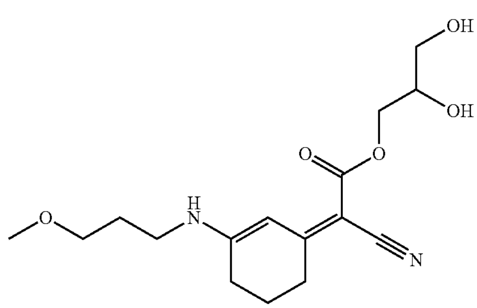 [SMILES: COCCCNC1=C/C(=C(/C#N)C(=O)OCC(O)CO)CCC1] |
| 41 | 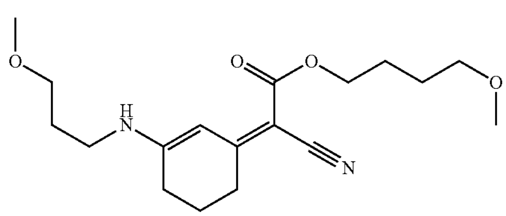 [SMILES: COCCCCOC(=O)/C(C#N)=C1\C=C(NCCCOC)CCC1] |
| 42 | 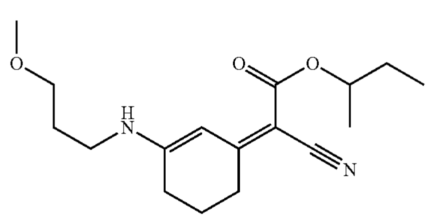 [SMILES: CCC(C)OC(=O)/C(C#N)=C1\C=C(NCCCOC)CCC1] |

TABLE A-continued
| Compound | Structure |
|---|---|
| 43 | 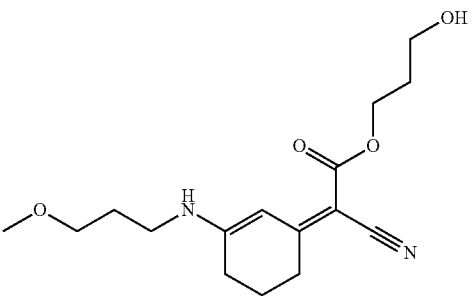 [SMILES: COCCCNC1=C/C(=C(/C#N)C(=O)OCCCO)CCC1] |
| 44 | 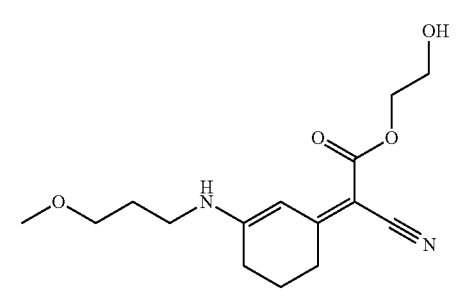 [SMILES: COCCCNC1=C/C(=C(/C#N)C(=O)OCCO)CCC1] |
| 45 | 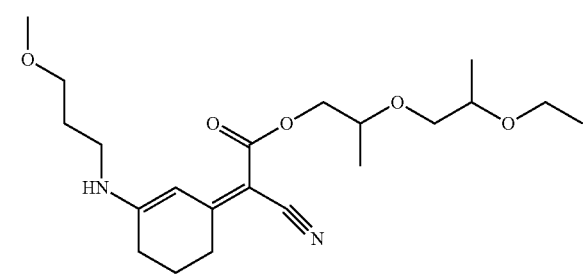 [SMILES: CCOC(C)COC(C)COC(=O)/C(C#N)=C1\C=C(NCCCOC)CCC1] |
| 46 | 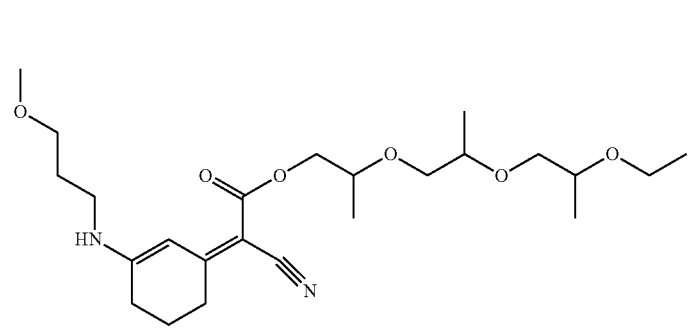 [SMILES: CCOC(C)COC(C)COC(C)COC(=O)/C(C#N)=C1\C=C(NCCCOC)CCC1] |
| 47 | 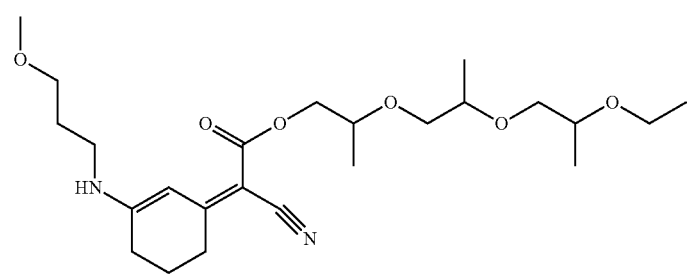 [SMILES: CCOC(C)COC(C)COC(C)COC(=O)/C(C#N)=C1\C=C(NCCCOC)CCC1] | and those corresponding to formula (3) below and also the E/E- or E/Z-geometrical isomer forms thereof:

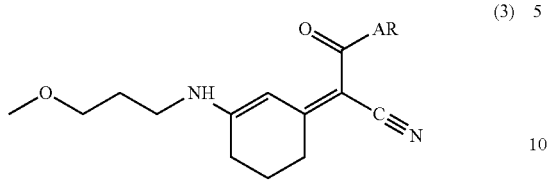
(3)

in which

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, said groups possibly being interrupted with one or more O; and b) at least one oily phase comprising at least one amide selected from the group of amides of formula (4)

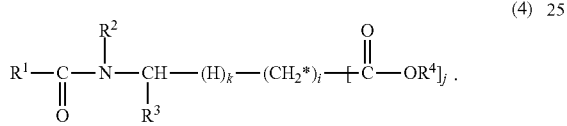
(4)

in which:

the $R^1$ radical represents a linear or branched $C_1$-$C_4$ alkyl radical; a linear or branched $C_2$-$C_4$ alkenyl radical, or an aryl radical", limits included;

the $R^2$, $R^3$ and $R^4$ radicals, which may be identical or different, represent saturated or unsaturated, aliphatic, cycloaliphatic or cyclic, optionally functionalized, monovalent hydrocarbon-based radicals containing from 1 to 30 carbon atoms, limits included;

k is 0 or 1;

i is an integer from 0 to 2;

j is 0 or 1;

with the proviso that:
when j=1 then k is 0 and
$R^1$ represents a linear or branched $C_1$-$C_4$ alkyl radical; a linear or branched $C_2$-$C_4$ alkenyl radical, or an aryl radical;
$R^2$ represent a hydrogen atom or a linear or branched $C_1$-$C_6$ alkyl group;
$R^3$ represents a hydrogen atom or a linear or branched $C_1$-$C_6$ alkyl group;
$R^4$ represents a linear or branched $C_1$-$C_{10}$ alkyl radical, a linear or branched $C_2$-$C_{10}$ alkenyl radical or a sterol residue;
or with the proviso that:
when j=0, then i=0 and k=1 and $R^1$ represents an unsaturated cyclic hydrocarbon-based radical, which is optionally substituted.

2. The composition according to claim 1, wherein the at least one merocyanine is chosen from the following compounds and also the E/E- or E/Z-geometrical isomer forms thereof:

TABLE A

| Compound | Structure |
|---|---|
| 1 | 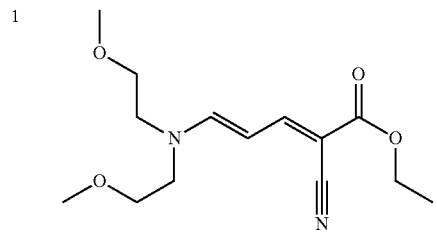 |
| 2 | 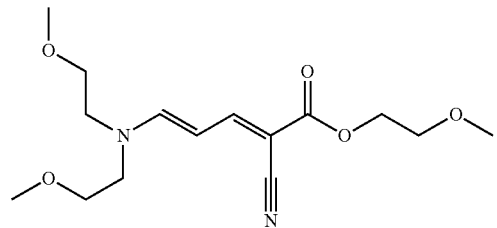 |
| 3 | 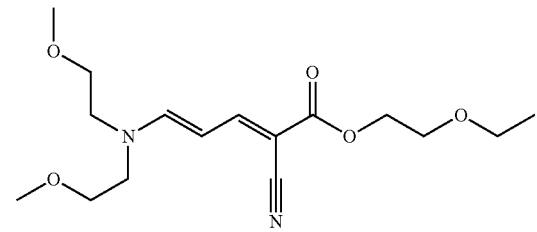 [SMILES: CCOCCOC(=O)/C(C#N)=C/C=C/N(CCOC)CCOC] |

TABLE A-continued
| Compound | Structure |
|---|---|
| 4 | 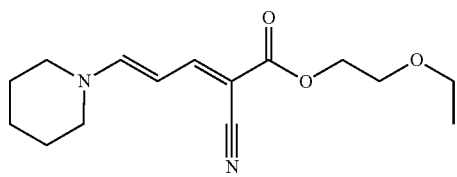 [SMILES: CCOCCOC(=O)/C(C#N)=C/C=C/N1CCCCC1] |
| 5 | 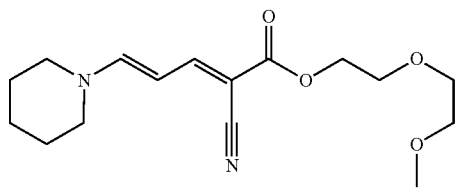 [SMILES: COCCOCCOC(=O)/C(C#N)=C/C=C/N1CCCCC1] |
| 6 | 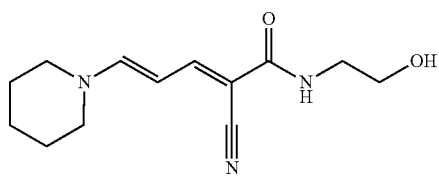 [SMILES: N#C/C(=C\C=C\N1CCCCC1)C(=O)NCCO] |
| 7 | 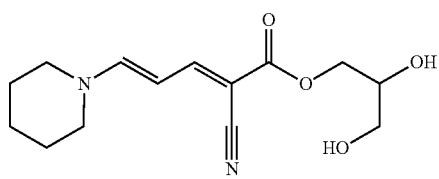 [SMILES: N#C/C(=C\C=C\N1CCCCC1)C(=O)OCC(O)CO] |
| 8 | 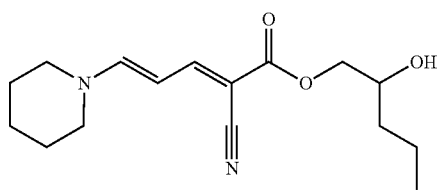 [SMILES: CCCC(O)COC(=O)/C(C#N)=C/C=C/N1CCCCC1] |
| 9 | 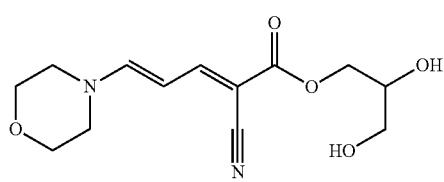 [SMILES: N#C/C(=C\C=C\N1CCOCC1)C(=O)OCC(O)CO] |
| 10 | 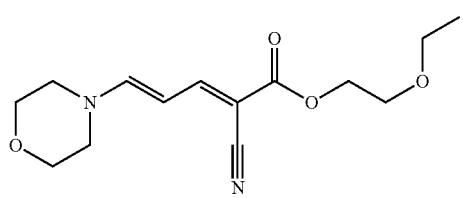 [SMILES: CCOCCOC(=O)/C(C#N)=C/C=C/N1CCOCC1] |
| 11 | 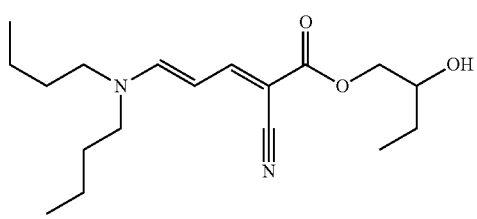 [SMILES: CCCCN(/C=C/C=C(\C#N)C(=O)OCC(O)CC)CCCC] |

TABLE A-continued
| Compound | Structure |
|---|---|
| 12 | 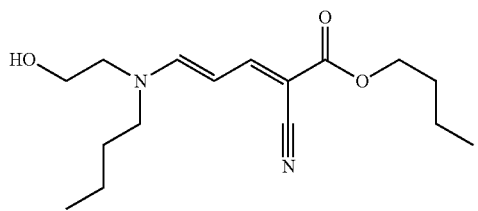 [SMILES: CCCCOC(=O)/C(C#N)=C/C=C/N(CCO)CCCC] |
| 13 | 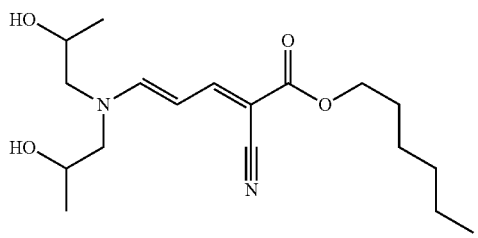 |
| 14 | 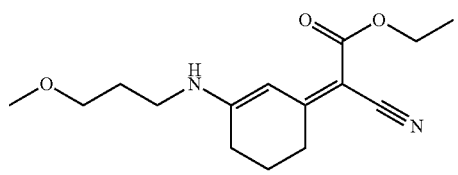 [SMILES: CCOC(=O)/C(C#N)=C1\C=C(NCCCOC)CCC1] |
| 15 | 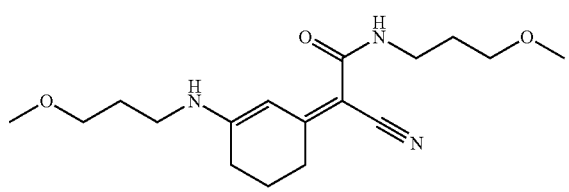 |
| 16 | 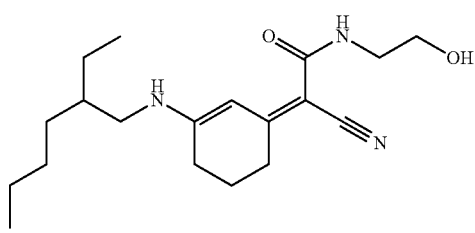 [SMILES: CCCCC(CC)CNC1=C/C(=C(/C#N)C(=O)NCCO)CCC1] |
| 17 | 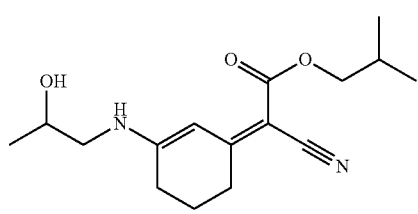 [SMILES: CC(C)COC(=O)/C(C#N)=C1\C=C(NCC(C)O)CCC1] |
| 18 | 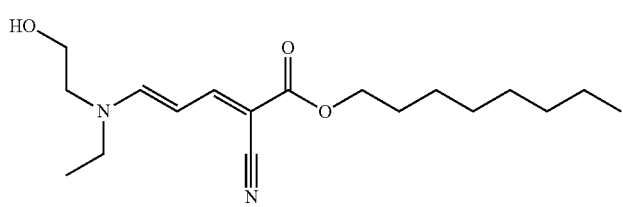 [SMILES: CCCCCCCCOC(=O)/C(C#N)=C/C=C/N(CC)CCO] |

TABLE A-continued
| Compound | Structure |
|---|---|
| 19 | 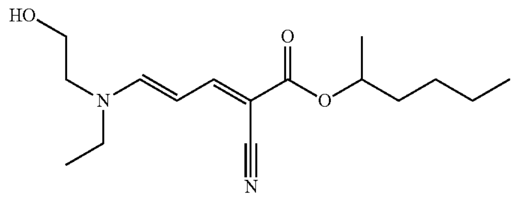 [SMILES: CCCCC(C)OC(=O)/C(C#N)=C/C=C/N(CC)CCO] |
| 20 | 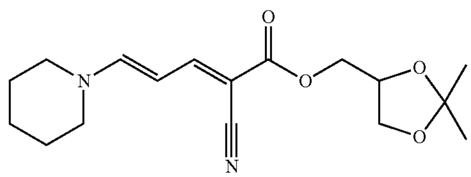 [SMILES: CC1(C)OCC(COC(=O)/C(C#N)=C/C=C/N2CCCCC2)O1] |
| 21 | 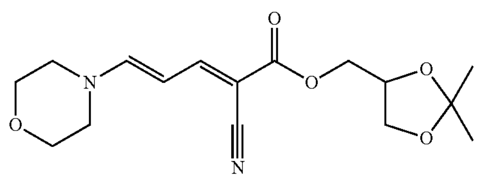 [SMILES: CC1(C)OCC(COC(=O)/C(C#N)=C/C=C/N2CCOCC2)O1] |
| 22 | 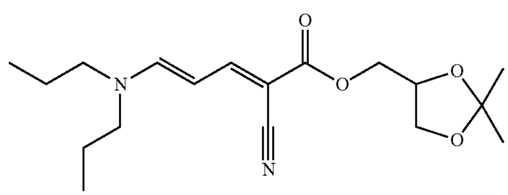 [SMILES: CCCN(/C=C/C=C(\C#N)C(=O)OCC1COC(C)(C)O1)CCC] |
| 23 | 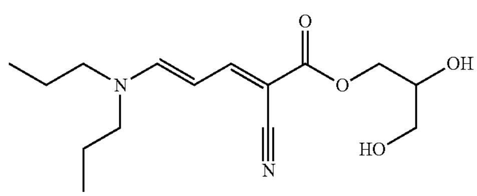 [SMILES: CCCN(/C=C/C=C(\C#N)C(=O)OCC(O)CO)CCC] |
| 24 | 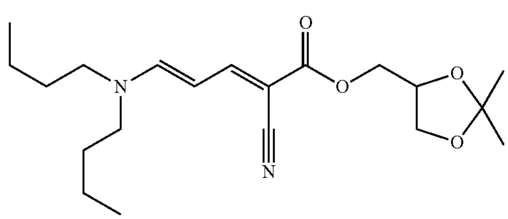 [SMILES: CCCCN(/C=C/C=C(\C#N)C(=O)OCC1COC(C)(C)O1)CCCC] |
| 25 | 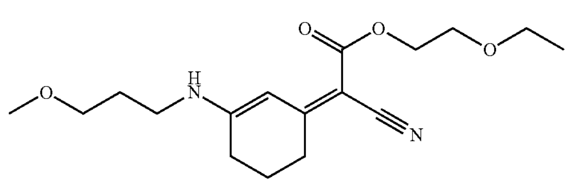 [SMILES: CCOCCOC(=O)/C(C#N)=C1\C=C(NCCCOC)CCC1] |
| 26 | 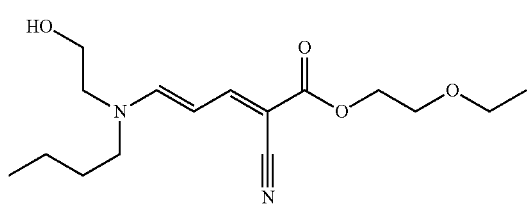 [SMILES: CCCCN(/C=C/C=C(\C#N)C(=O)OCCOCC)CCO] |
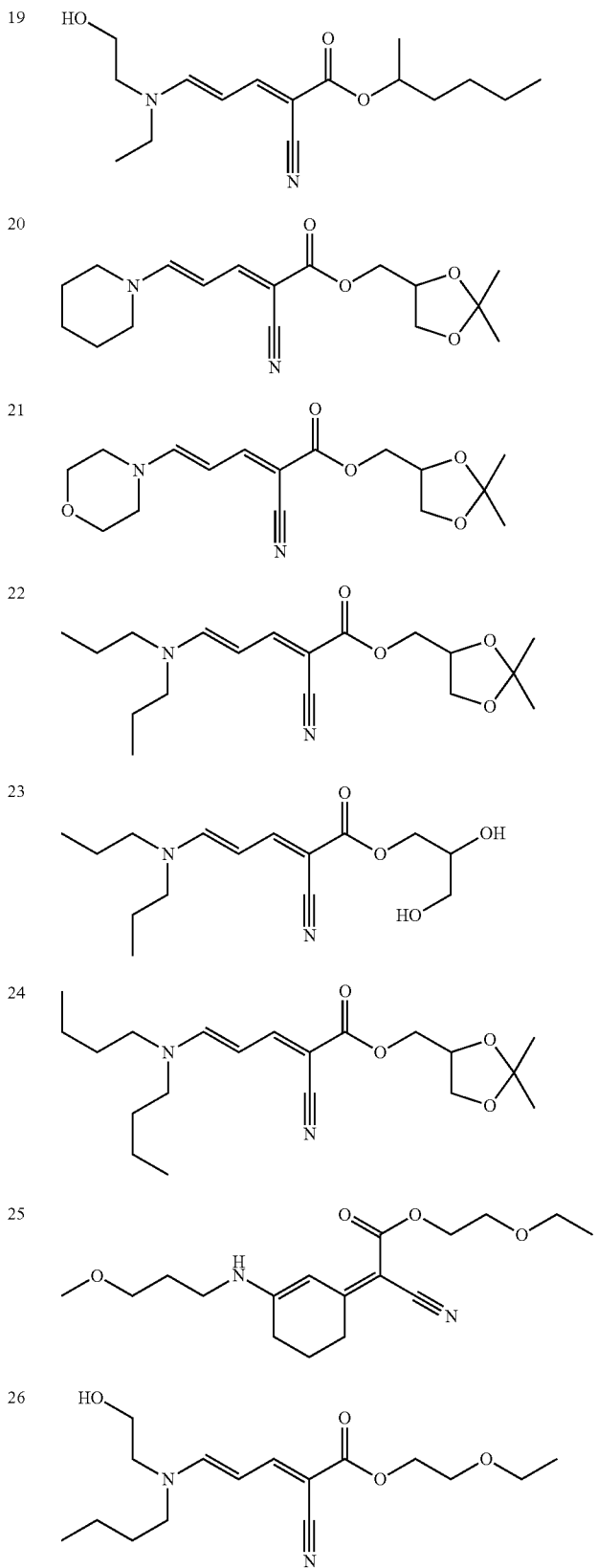

TABLE A-continued
| Compound | Structure |
|---|---|
| 27 | 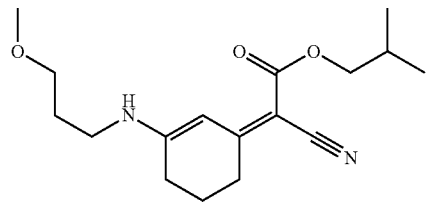 [SMILES: COCCCNC1=C/C(=C(/C#N)C(=O)OCC(C)C)CCC1] |
| 28 | 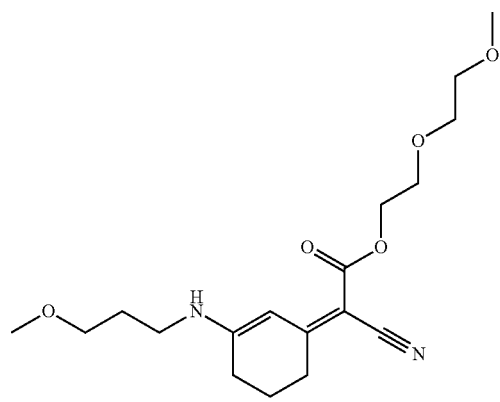 |
| 29 | 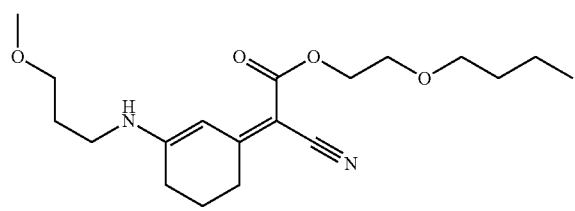 [SMILES: CCCCOCCOC(=O)/C(C#N)=C1\C=C(NCCCOC)CCC1] |
| 30 | 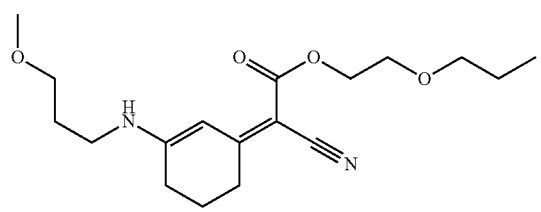 [SMILES: CCCOCCOC(=O)/C(C#N)=C1\C=C(NCCCOC)CCC1] |
| 31 | 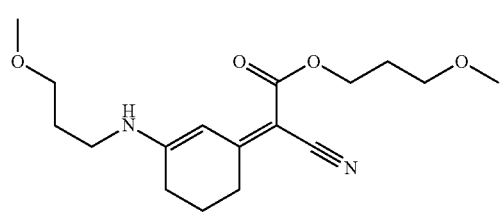 |
| 32 | 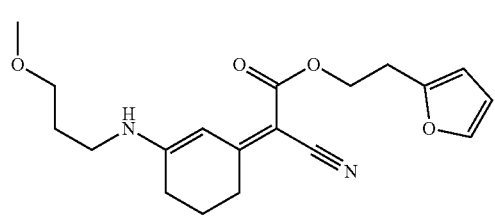 [SMILES: COCCCNC1=C/C(=C(/C#N)C(=O)OCCc2ccco2)CCC1] |

TABLE A-continued
| Compound | Structure |
|---|---|
| 33 | 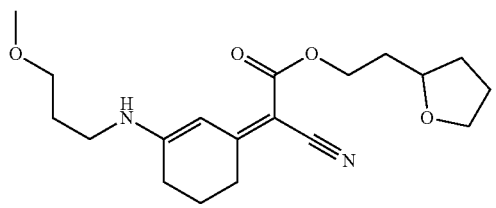 [SMILES: COCCCNC1=C/C(=C(/C#N)C(=O)OCCC2CCCO2)CCC1] |
| 34 | 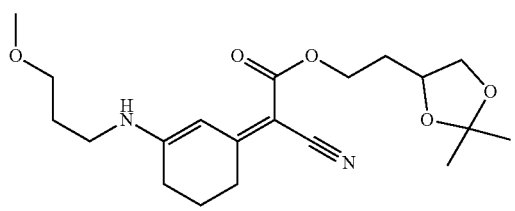 [SMILES: COCCCNC1=C/C(=C(/C#N)C(=O)OCCC2COC(C)(C)O2)CCC1] |
| 35 | 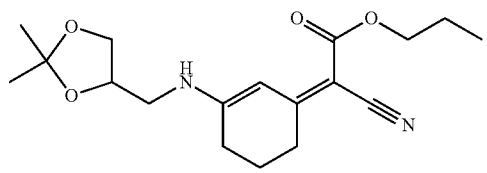 [SMILES: CCCOC(=O)/C(C#N)=C1\C=C(NCC2COC(C)(C)O2)CCC1] |
| 36 | 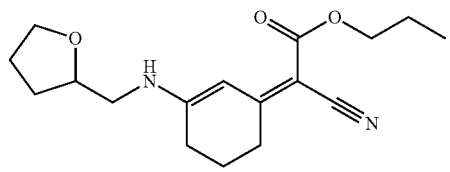 [SMILES: CCCOC(=O)/C(C#N)=C1\C=C(NCC2CCCO2)CCC1] |
| 37 | 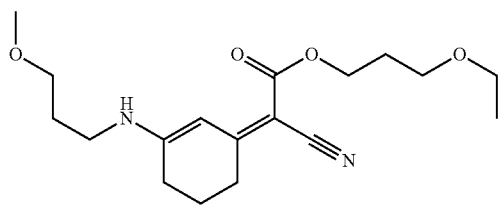 [SMILES: CCOCCCOC(=O)/C(C#N)=C1\C=C(NCCCOC)CCC1] |
| 38 | 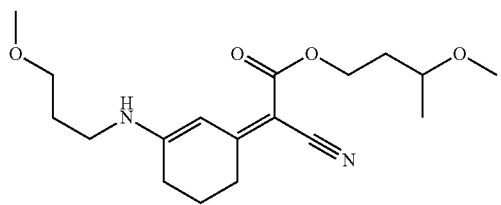 [SMILES: COCCCNC1=C/C(=C(/C#N)C(=O)OCCC(C)OC)CCC1] |
| 39 | 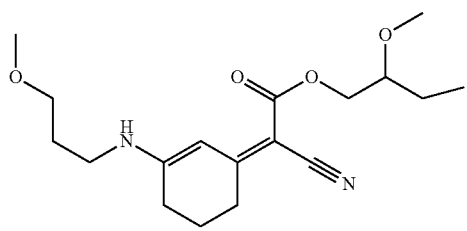 [SMILES: CCC(COC(=O)/C(C#N)=C1\C=C(NCCCOC)CCC1)OC] |

TABLE A-continued
| Compound | Structure |
|---|---|
| 40 | 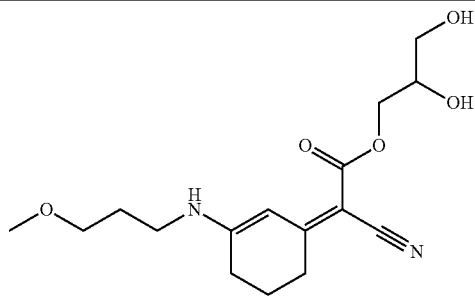 |
| 41 | 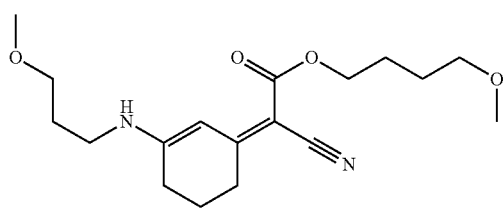 [SMILES: COCCCCOC(=O)/C(C#N)=C1\C=C(NCCCOC)CCC1] |
| 42 | 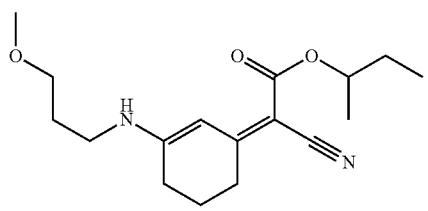 [SMILES: CCC(C)OC(=O)/C(C#N)=C1\C=C(NCCCOC)CCC1] |
| 43 | 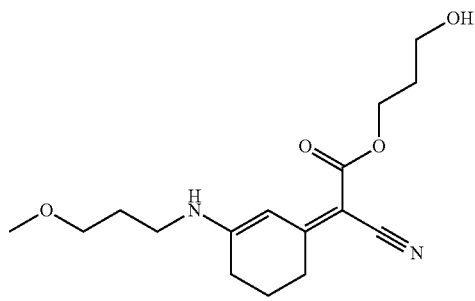 [SMILES: COCCCNC1=C/C(=C(/C#N)C(=O)OCCCO)CCC1] |
| 44 | 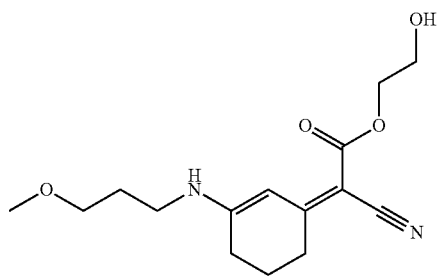 [SMILES: COCCCNC1=C/C(=C(/C#N)C(=O)OCCO)CCC1] |
| 45 | 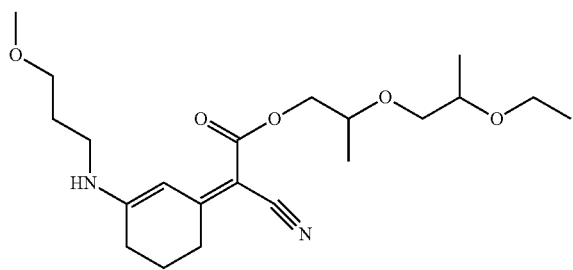 [SMILES: CCOC(C)COC(C)COC(=O)/C(C#N)=C1\C=C(NCCCOC)CCC1] |

TABLE A-continued

| Compound | Structure |
|---|---|
| 46 | 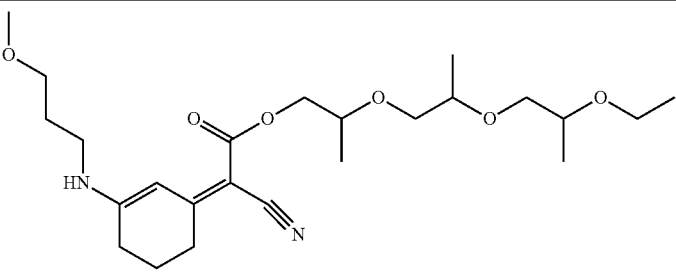 |
| 47 | 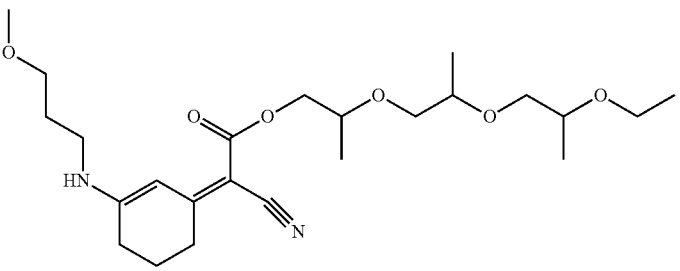 [SMILES: CCOC(C)COC(C)COC(C)COC(=O)/C(C#N)=C1\C=C(NCCCOC)CCC1] |

3. The composition according to claim 1, wherein the at least one merocyanine is chosen from those corresponding to formula (3) below and also the E/E- or E/Z-geometrical isomer forms thereof:

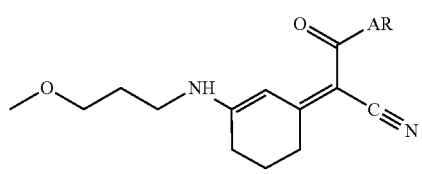

(3)

in which

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, said groups possibly being interrupted with one or more O.

4. The composition according to claim 1, wherein at least one merocyanine is chosen from the following compounds and also the E/E- or E/Z-geometrical isomer forms thereof:

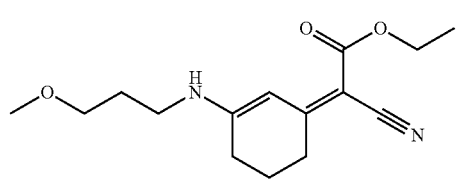

ethyl (2Z)-cyano{3-[(3-methoxypropyl)amino]cyclohex-2-en-1-ylidene}ethanoate

14

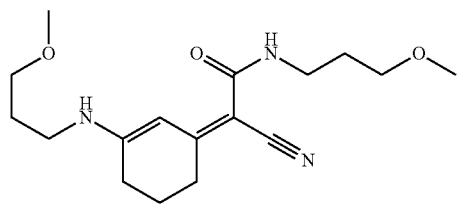

(2Z)-2-cyano-N-(3-methoxypropyl)-2-{3-[(3-methoxypropyl)amino]cyclohex-2-en-1-ylidene}ethanamide

15

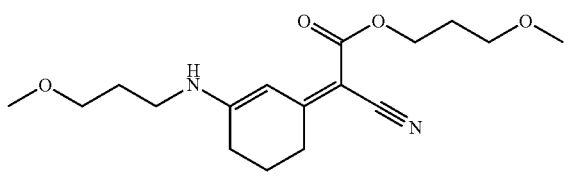

2-ethoxyethyl (2Z)-cyano{3-[(3-methoxypropyl)amino]cyclohex-2-en-1-ylidene}ethanoate

25

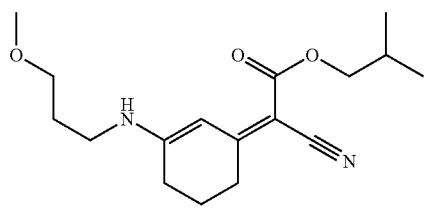

2-methylpropyl (2Z)-cyano{3-[(3-methoxypropyl)amino]cyclohex-2-en-1-ylidene}ethanoate

27

-continued

29

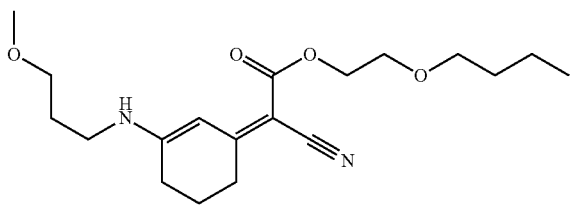

2-butoxyethyl (2Z)-cyano{3-[(3-methoxypropyl)amino]cyclohex-2-en-1-ylidene}ethanoate

31

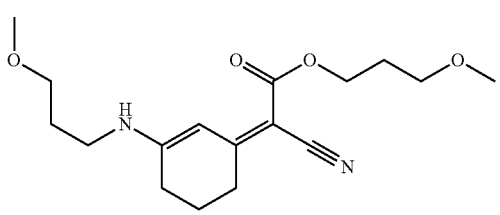

3-methoxypropyl (2Z)-cyano{3-[(3-methoxypropyl)amino]cyclohex-2-en-1-ylidene}ethanoate

37

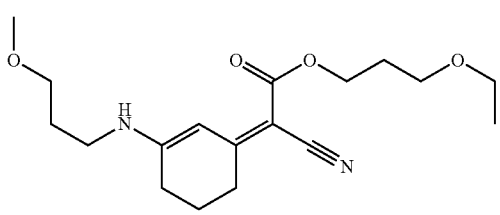

3-ethoxypropyl (2Z)-cyano{3-[(3-methoxypropyl)amino]cyclohex-2-en-1-ylidene}ethanoate 5. The composition according to claim 4, wherein the at least one merocyanine is the compound 2-ethoxyethyl (2Z)-cyano{3-[(3-methoxypropyl)amino]cyclohex-2-en-1-ylidene}ethanoate (25) in its E/Z geometrical configuration having the following structure:

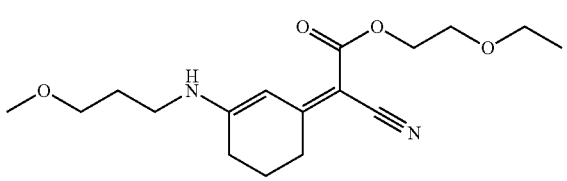 [SMILES: CCOCCOC(=O)/C(C#N)=C1\C=C(NCCCOC)CCC1]

and/or the E/E form having the following structure:

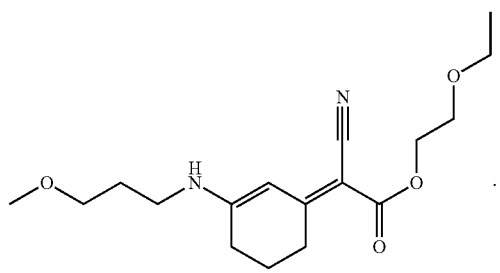 [SMILES: CCOCCOC(=O)/C(C#N)=C1/C=C(NCCCOC)CCC1]

6. The composition according to claim 1, wherein the at least one merocyanine compound is present in a concentration ranging from 0.1% to 10% by weight relative to the total weight of the composition.

7. The composition according to claim 1, wherein the at least one amide is chosen from:

N-acetyl N-butylaminopropionate having the formula below:

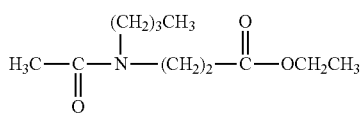

N,N-diethyltoluamide having the formula:

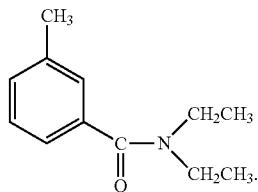

8. The composition according to claim 1, wherein the at least one amide is present in concentrations ranging from 0.1% to 95% by weight relative to the total weight of the composition.

9. The composition according to claim 1, characterized in that it also comprises an additional UV-screening agent.

10. A non-therapeutic cosmetic process for caring for and/or making up a keratin material, comprising the application, to the surface of said keratin material, of at least one composition as defined in claim 1.

11. A non-therapeutic cosmetic process for treating the signs of ageing of a keratin material, comprising the application, to the surface of the keratin material, of at least one composition as defined in claim 1.

12. The composition according to claim 1, wherein the at least one merocyanine compound is present in a concentration ranging from 0.2% to 5% by weight relative to the total weight of the composition.

13. The composition according to claim 12, wherein the at least one amide is present in concentrations ranging from 0.5% to 50% by weight relative to the total weight of the composition.

14. The composition according to claim 12, wherein the at least one amide is present in concentrations ranging from 1% to 20% by weight relative to the total weight of the composition.

15. The composition according to claim 1, wherein the at least one amide is present in concentrations ranging from 0.5% to 50% by weight relative to the total weight of the composition.

16. The composition according to claim 1, wherein the at least one amide is present in concentrations ranging from 1% to 20% by weight relative to the total weight of the composition.

17. The composition according to claim 4, wherein the at least one merocyanine compound is present in a concentration ranging from 0.1% to 10% by weight relative to the total weight of the composition.

18. The composition according to claim 5, wherein the at least one merocyanine compound is present in a concentration ranging from 0.1% to 10% by weight relative to the total weight of the composition.

19. The composition according to claim 5, wherein the at least one merocyanine compound is present in a concentration ranging from 0.2% to 5% by weight relative to the total weight of the composition.

20. The composition according to claim 7, wherein the at least one amide is present in concentrations ranging from 1% to 20% by weight relative to the total weight of the composition.

21. The composition according to claim 5, wherein the at least one amide is chosen from:

N-acetyl N-butylaminopropionate having the formula below:

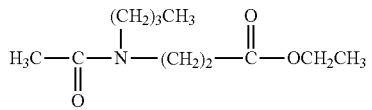

N,N-diethyltoluamide having the formula:

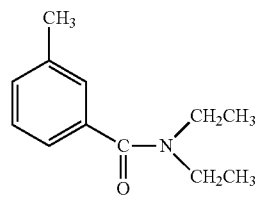

* * * * *